United States Patent
Norviel et al.

(10) Patent No.: US 12,109,229 B2
(45) Date of Patent: *Oct. 8, 2024

(54) TREATMENT OF NEURODEGENERATIVE DISEASE WITH SODIUM CHLORITE

(71) Applicants: Neuvivo, Inc., Palo Alto, CA (US); The Regents of the University of California, Oakland, CA (US)

(72) Inventors: Vernon A. Norviel, San Diego, CA (US); Michael S. McGrath, Meadow Vista, CA (US)

(73) Assignees: NEUVIVO, INC., Palo Alto, CA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/441,600

(22) Filed: Feb. 14, 2024

(65) Prior Publication Data

US 2024/0261324 A1 Aug. 8, 2024

Related U.S. Application Data

(63) Continuation of application No. 18/095,199, filed on Jan. 10, 2023, now Pat. No. 11,938,148, which is a continuation of application No. 17/823,489, filed on Aug. 30, 2022, now Pat. No. 11,938,147, which is a continuation of application No. 15/772,317, filed as application No. PCT/US2016/059915 on Nov. 1, 2016, now abandoned.

(60) Provisional application No. 62/249,846, filed on Nov. 2, 2015.

(51) Int. Cl.
*A61K 33/20* (2006.01)
*A61P 25/28* (2006.01)

(52) U.S. Cl.
CPC .............. *A61K 33/20* (2013.01); *A61P 25/28* (2018.01)

(58) Field of Classification Search
CPC ...................................................... A61K 33/20
See application file for complete search history.

(56) References Cited

U.S. PATENT DOCUMENTS

| | | |
|---|---|---|
| 7,105,183 B2 | 9/2006 | McGrath |
| 8,029,826 B2 | 10/2011 | McGrath |
| 8,067,035 B2 | 11/2011 | Boulanger et al. |
| 8,231,856 B2 | 7/2012 | Boulanger et al. |
| 8,501,244 B2 | 8/2013 | Boulanger et al. |
| 9,266,734 B2 | 2/2016 | Boulanger et al. |
| 9,364,501 B2 | 6/2016 | McGrath |
| 9,579,346 B2 | 2/2017 | McGrath et al. |
| 9,839,650 B2 | 12/2017 | Boulanger et al. |
| 11,938,147 B2 | 3/2024 | Norviel et al. |
| 11,938,148 B2 | 3/2024 | Norviel et al. |
| 11,938,149 B2 | 3/2024 | Norviel et al. |
| 11,938,150 B2 | 3/2024 | Norviel et al. |
| 2006/0051790 A1 | 3/2006 | Geschwind et al. |
| 2007/0145328 A1 | 6/2007 | Boulanger et al. |
| 2011/0086894 A1 | 4/2011 | Bowser |
| 2012/0134929 A1 | 5/2012 | McGrath et al. |
| 2012/0295296 A1 | 11/2012 | McGrath |
| 2014/0147856 A1 | 5/2014 | Forsyth et al. |
| 2014/0178420 A1 | 6/2014 | Goldberg et al. |
| 2015/0258069 A1 | 9/2015 | Voudouris |
| 2019/0060359 A1 | 2/2019 | Norviel et al. |
| 2023/0190790 A1 | 6/2023 | Azhir et al. |

FOREIGN PATENT DOCUMENTS

| | | |
|---|---|---|
| AU | 2011205095 A1 | 8/2011 |
| WO | WO-2008042190 A2 | 4/2008 |
| WO | WO-2014057880 A1 | 4/2014 |
| WO | WO-2015006489 A1 | 1/2015 |
| WO | WO-2015175974 A1 | 11/2015 |
| WO | WO-2017079161 A2 | 5/2017 |
| WO | WO-2023060097 A1 | 4/2023 |

OTHER PUBLICATIONS

Alzforum. In ALS, Respiratory Measure Predicts Pace of Disease. Webpage. https://www.alzforum.org/news/research-news/als-respiratory-measure-predicts-pace-disease. Dec. 1, 2017.
Burdo et al., Soluble CD163 Made by Monocyte/Macrophages Is a Novel Marker of HIV Activity in Early and Chronic Infection Prior to and After Anti-retroviral Therapy. The Journal of Infectious Diseases 204:154-163 (2011).
Cederbaum et al., The ALSFRS-R: a revised ALS functional rating scale that incorporates assessments of respiratory function. BDNF ALS Study Group (Phase III). J Neurol Sci 169(1-2):13-21 (1999).
Cellura et al. Factors affecting the diagnostic delay in amyotrophic lateral sclerosis. Clin Neurol Neurosurg 114(6):550-554 (2012).
Co-pending U.S. Appl. No. 18/441,597, inventors Norviel; Vernon A. et al., filed Feb. 14, 2024.
Co-pending U.S. Appl. No. 18/441,611, inventors Norviel; Vernon A. et al., filed Feb. 14, 2024.
Co-pending U.S. Appl. No. 18/441,621, inventors Norviel; Vernon A. et al., filed Feb. 14, 2024.
Dyken et al. Neurodegenerative diseases of infancy and childhood. Ann Neurol. 13(4):351-64 (1983).

(Continued)

*Primary Examiner* — Yong S. Chong
(74) *Attorney, Agent, or Firm* — WILSON SONSINI GOODRICH & ROSATI

(57) ABSTRACT

The present invention provides a method of treating frontotemporal dementia, or a childhood genetic neurodegenerative disease such as Ataxia Telangiectasia (A-T), or neurodegenerative diseases such as Parkinson's disease or neuropsychiatric diseases comprising administering to a subject in need thereof an effective amount of chlorite composition, such as sodium chlorite. The present invention thereby provides a method of modulating the immune system in a subject in need thereof. Described herein are methods of administration and treatment.

14 Claims, 16 Drawing Sheets

(56) References Cited

OTHER PUBLICATIONS

Galimberti et al. Inflammatory molecules in Frontotemporal Dementia: Cerebrospinal fluid signature of progranulin mutation carriers. Brain Behavior and Immunity 49:182-187 (2015).
Joyce et al. Electrodiagnosis in Amyotrophic Lateral Sclerosis. PM R 5(5 Suppl):S89-95 (2013).
Kale et al. Osteopontin signaling upregulates cyclooxygenase-2 expression in tumor-associated macrophages leading to enhanced angiogenesis and melanoma growth via a9b1 integrin. Oncogene 33:2295-2306(2014).
Khazen et al. Expression of macrophage-selective markers in human and rodent adipocytes. FEBS Lett. 579(25):5631-4 (2005).
Luo et al., Bioluminescence analysis of Smad-dependent TGF-beta signaling in live mice. Methods Mol Biol 574:193-202 (2009).
Luo et al., Bioluminescence imaging of Smad signaling in living mice shows correlation with excitotoxic neurodegeneration. PNAS 103(48): 18326-18331 (2006).
Mackenzie. The neuropathology and clinical phenotype of FTD with progranulin mutations. Acta Neuropathol. 114(1):49-54 (2007).
Miller et al., NP001 regulation of macrophage activation markers in ALS: A phase I clinical and biomaker study. Amyotrophic Lateral Sclerosis and Frontotemporal Degeneration 15:601-609 (2014).
Miller et al. Phase 2B randomized controlled trial of NP001 in amyotrophic lateral sclerosis: Pre-specified and post hoc analyses. Muscle Nerve. 66(1):39-49 (2022).
Miller et al., Randomized phase 2 trial of NP001-a novel immune regulator: Safety and early efficacy in ALS. Neurol Neuroimmunol Neuroinflamm 2:e100 (2015).
Minami et al., Progranulin protects against amyloid β deposition and toxicity in Alzheimer's disease mouse models. Nat Med 20(10):1157-1164 (2014).
Nzwalo et al. Delayed diagnosis in ALS: the problem continues. J Neurol Sci 343(1-2):173-175 (2014).
Orsini et al., Frontotemporal dementia in amyotrophic lateral sclerosis: from rarity to reality? Neurology International 8:6534:1-3 (2016).
PCT/US2016/059915 International Search Report and Written Opinion dated Apr. 17, 2017.
PCT/US2022/077557 International Search Report and Written Opinion dated Mar. 14, 2023.
Qin et al., NADPH oxidase and aging drive microglial activation, oxidative stress, and dopaminergic neurodegeneration following systemic LPS administration. Glia 61(6):855-868 (2013).
Simeonovska et al. Differential diagnosis between Bulbospinal muscular atrophy—Kennedy's disease and Amyotrophic lateral sclerosis. Acta Medica Medianae 58(2):77-81 (2019).
Thomas Sciencific Lab Supplies and Equipment. https://www.thomassci.com/Laboratory-Supplies/Sample-Vials/JDepyrogenated-Sterile-Empty-Vials (8 pgs.) (2018).
Thomas Scientific. https://www.thomassci.com/Laboratory-Supplies/Sampling-Serum-Bottles/_/Sterile-Empty-Vial-Clear?q=20A00M599 (2023).
Uher et al., An inflammatory biomarker as a differential predictor of outcome of depression treatment with escitalopram and nortriptyline. Am J Psychiatry 171(12):1278-1286 (2014).
U.S. Appl. No. 15/772,317 Final Office Action dated Nov. 2, 2020.
U.S. Appl. No. 15/772,317 Office Action dated Feb. 14, 2020.
U.S. Appl. No. 15/772,317 Office Action dated Jul. 22, 2021.
U.S. Appl. No. 17/823,489 Office Action dated Apr. 6, 2023.
U.S. Appl. No. 17/823,489 Office Action dated Aug. 18, 2018.
U.S. Appl. No. 17/823,489 Office Action dated Jun. 14, 2023.
U.S. Appl. No. 17/823,489 Office Action dated Nov. 20, 2023.
U.S. Appl. No. 18/095,199 Office Action dated Apr. 28, 2023.
U.S. Appl. No. 18/095,199 Office Action dated Aug. 18, 2023.
U.S. Appl. No. 18/095,199 Office Action dated Jun. 14, 2023.
U.S. Appl. No. 18/095,199 Office Action dated Nov. 20, 2023.
U.S. Appl. No. 18/095,202 Office Action dated Aug. 24, 2023.
U.S. Appl. No. 18/095,202 Office Action dated Jun. 14, 2023.
U.S. Appl. No. 18/095,202 Office Action dated May 18, 2023.
U.S. Appl. No. 18/095,202 Office Action dated Nov. 21, 2023.
U.S. Appl. No. 18/095,205 Office Action dated Aug. 24, 2023.
U.S. Appl. No. 18/095,205 Office Action dated Jun. 14, 2023.
U.S. Appl. No. 18/095,205 Office Action dated Mar. 24, 2023.
U.S. Appl. No. 18/095,205 Office Action dated Nov. 21, 2023.
Walker et al. The association of mid-to late-life systemic inflammation with white matter structure in older adults: The ARIC Study. Neurobiol Aging 68:26-33 (2018).
Yin et al., Exaggerated inflammation, impaired host defense, and neurophathology in progranulin-deficient mice. J. Exp. Med. 207(1):117-128 (2009).
Zhang et al. Macrophage-Targeted Sodium Chlorite (NP001) Slows Progression of Amyotrophic Lateral Sclerosis (ALS) through Regulation of Microbial Translocation. Biomedicines 10(11):2907 (2022).
Kim, Young Min et al. Slow Injection of Nefopam Reduces Pain Intensity Associated With Intravenous Injection: a Prospective Randomized Trial. Journal of Anesthesia vol. 28(3):399-406 (2014).

TREATMENT OF NEURODEGENERATIVE DISEASE WITH SODIUM CHLORITE

INCORPORATION BY REFERENCE

This application is a continuation of U.S. Application No. 18/095,199 filed Jan. 10, 2023, which is a continuation of U.S. Application No. 17/823,489 filed Aug. 30, 2022, which is a continuation of U.S. application Ser. No. 15/772,317, filed Apr. 30, 2018, which is a § 371 U.S. National Stage Entry of International Application No. PCT/US16/59915, filed Nov. 1, 2016, which claims the benefit to U.S. Provisional Application No. 62/249,846, filed Nov. 2, 2015, which are incorporated herein by reference in their entirety.

BACKGROUND OF THE INVENTION

Neurodegenerative disease encompasses a long list of distinct conditions characterized by progressive neuropathy and loss of neurons in motor, sensory, and/or cognitive systems. Well-known neurodegenerative diseases include Alzheimer's disease (AD), Pick's disease, Lewy body dementia, Huntington's disease and Parkinson's disease. However, there are a myriad of lesser known and rare neurodegenerative diseases. Patients suffering from these rare conditions often face few treatment options.

Ataxia Telangiectasia (A-T), also referred to as Louis-Bar syndrome, is one of many rare, neurodegenerative, inherited diseases that affect many parts of the body and cause severe disability. Ataxia refers to poor coordination and telangiectasia to small dilated blood vessels, which are hallmarks of the disease. A-T is caused, at least partially, by a defect in the ATM gene, which is responsible for recognizing and correcting errors in duplicating DNA when cells divide, and in destroying the cells when the errors are not corrected. The protein from the ATM gene normally repairs double-stranded DNA breaks. A-T affects the cerebellum (the motor coordination control center) and also weakens the immune system in about 70% of the cases, leading to respiratory disorders and increased risk of other diseases. It first appears in early childhood at around the toddler stage with symptoms such as lack of balance, slurred speech, and increased infections. Those with A-T usually die in their teens or early adulthood. A-T is one of several childhood genetic disorders which results in neurological abnormalities or degeneration. Some of the most devastating symptoms of such diseases are a result of progressive cerebellar degeneration, characterized by neuronal cell death in the brain and/or central nervous system. Current treatments of A-T and other childhood genetic neurodegenerative disorders are symptomatic and supportive, but are lacking in efficacy. Thus, there remains a need for alternative treatments for Ataxia Telangiectasia and other childhood genetic neurodegenerative diseases.

Frontotemporal dementia (FTD) or frontotemporal lobar degeneration (FTLD) is an umbrella term for a diverse group of uncommon neurodegenerative disorders that primarily affect the frontal and temporal lobes of the brain—the areas generally associated with personality, behavior and language. FTD is the most common form of dementia that occurs in individuals below the age of 60. Approximately ⅓ has a genetic basis for the disease whereas the other ⅔ has a "sporadic" form. The disease involves the evolution of neurodegenerative disease activity in the frontal and or temporal regions of the brain starting around 50 years after birth. After diagnosis the median survival is less than 5 years, substantially less if the patients also have motor neuron involvement. Portions of these lobes atrophy or shrink in FTD patients. Signs and symptoms vary, depending upon the portion of the brain affected, include, but are not limited to loss of empathy, repetitive compulsive behavior, tremor, rigidity and muscle spasms. FTD tends to occur at a relatively young age for a neurodegenerative disease, often in the 40's or 50's, which can be financially crippling for families of patients, and progresses at a rapid rate. Patients suffering from the disease can survive between 2-10 years. Eventually patients will need 24-hour care for daily function.

Currently, there is no cure for FTD. Treatments, including serotonin reuptake inhibitors, are available to manage the behavioral symptoms. Although AD and FTD share some symptoms, FTD does not respond to pharmacological agents used to treat AD.

SUMMARY OF THE INVENTION

Disclosed herein are methods of treating a childhood neurodegenerative disease comprising administering to a subject in need thereof an effective amount of a pharmaceutical composition comprising a pharmaceutically acceptable chlorite composition. The pharmaceutically acceptable chlorite composition may comprise sodium chlorite. The pharmaceutically acceptable chlorite composition may consist essentially of sodium chlorite and a buffer that is isotonic with a biological fluid of a human subject. The pharmaceutical composition may be suitable for parenteral administration or intravenous administration. The pharmaceutical composition may be isotonic with a biological fluid of the subject. The pharmaceutical composition may be administered by intravenous infusion over a period ranging from about 0.5 to about 4 hours. The pharmaceutical composition may be administered at least once per month for a period of at least a year. The pharmaceutical composition may be administered at least once per week for a period of at least one month. The pharmaceutically acceptable chlorite composition may be administered in an amount ranging from 0.1 to 10 mg/kg body weight. The amount may be about 1 to about 2 mg/kg body weight. The childhood neurodegenerative disease may be Ataxia Telangiectasia (A-T).

Further disclosed herein are methods of treating frontotemporal dementia (FTD) comprising administering to a subject in need thereof an effective amount of a pharmaceutical composition comprising a pharmaceutically acceptable chlorite composition. The pharmaceutically acceptable chlorite composition may comprise sodium chlorite. The pharmaceutically acceptable chlorite composition may consist essentially of sodium chlorite and a buffer that is isotonic with a biological fluid of a human subject. The pharmaceutical composition may be suitable for parenteral administration or intravenous administration. The pharmaceutical composition may be isotonic with a biological fluid of the subject. The pharmaceutical composition may be administered by intravenous infusion over a period ranging from about 0.5 to about 4 hours. The pharmaceutical composition may be administered at least once per month for a period of at least a year. The pharmaceutical composition may be administered at least once per week for a period of at least one month. The pharmaceutically acceptable chlorite composition may be administered in an amount ranging from 0.1 to 10 mg/kg body weight. The amount may be about 1 to about 2 mg/kg body weight. The method may reduce monocyte presence in the frontal and/or temporal lobes of a brain. The method may reduce monocyte production of inflammatory proteins in the frontal and/or temporal lobes of the brain. The method may reduce monocyte recruitment to the frontal and/or temporal lobes of the brain. The method may further comprise administering an antibiotic to the subject. The antibiotic may be specific to a bacterial species present in the subject that is causing expression of an lipopolysaccharide binding protein to be significantly higher than a subject not harboring a bacterial species that causes elevated expression of the lipopolysaccharide binding protein.

Disclosed herein are methods of treating Parkinson's disease comprising administering to a subject in need thereof an effective amount of a pharmaceutical composition comprising a pharmaceutically acceptable chlorite composition. The pharmaceutically acceptable chlorite composition may comprise sodium chlorite. The pharmaceutically acceptable chlorite composition may consist essentially of sodium chlorite and a buffer that is isotonic with a biological fluid of a human subject. The pharmaceutical composition may be suitable for parenteral administration or intravenous administration. The pharmaceutical composition may be isotonic with a biological fluid of the subject. The pharmaceutical composition may be administered by intravenous infusion over a period ranging from about 0.5 to about 4 hours. The pharmaceutical composition may be administered at least once per month for a period of at least a year. The pharmaceutical composition may be administered at least once per week for a period of at least one month. The pharmaceutically acceptable chlorite composition may be administered in an amount ranging from 0.1 to 13.5 mg/kg body weight. The amount may be about 1 to about 2 mg/kg body weight. The method may reduce monocyte activation in the midbrain. The method may reduce monocyte production of inflammatory proteins in the midbrain. The method may reduce monocyte recruitment to the midbrain.

Further disclosed herein are methods of treating a subject for Duchenne's muscular dystrophy (DMD) comprising administering to a subject in need thereof an effective amount of a pharmaceutical composition comprising a pharmaceutically acceptable chlorite composition. The pharmaceutically acceptable chlorite composition may comprise sodium chlorite. The pharmaceutically acceptable chlorite composition may consist essentially of sodium chlorite and a buffer that is isotonic with a biological fluid of a human subject. The pharmaceutical composition may be suitable for parenteral administration or intravenous administration. The pharmaceutical composition may be isotonic with a biological fluid of the subject. The pharmaceutical composition may be administered by intravenous infusion over a period ranging from about 0.5 to about 4 hours. The pharmaceutical composition may be administered at least once per month for a period of at least a year. The pharmaceutical composition may be administered at least once per week for a period of at least one month. The pharmaceutically acceptable chlorite composition may be administered in an amount ranging from 0.1 to 10 mg/kg body weight. The amount may be about 1 to about 2 mg/kg body weight.

Disclosed herein are method of preventing or delaying an onset of a symptom of a neurodegenerative disease, comprising administering a chlorite composition to a subject in need thereof, wherein the subject harbors a mutation in a gene, wherein the mutation in the gene is associated with the neurodegenerative disease; and wherein a level of a marker of the neurodegenerative disease is altered in a biological sample of the subject relative to a level of the marker in a control biological sample of a control subject. The method may comprise detecting the mutation in the biological sample of the subject. The method may comprise detecting the marker in the biological sample. The method may comprise quantifying the marker in the biological sample. The level of the marker may be at least 30% different than the level of the marker in the control sample of the control subject. The level of the marker may be at least 50% different than the level of the marker in the control sample of the control subject. The biological sample may be selected from a whole blood sample, a plasma sample, a serum sample, a urine sample, and a cerebrospinal fluid sample. The neurodegenerative disease may be selected from frontotemporal dementia, amyotrophic lateral sclerosis, or a condition in the spectrum thereof. The neurodegenerative disease may be Frontotemporal Dementia, Amyotrophic Lateral Sclerosis or a combination thereof, and the gene may be selected from c9orf72, microtubule associated protein tau, transactive response DNA binding protein 43 kDa, valosin containing protein, charged multivesicular body protein 2B, superoxide dismutase 1 gene, fused in sarcoma gene, and progranulin, and combinations thereof. The marker may be an inflammatory factor. The marker may be selected from CCL18, LBP, CD163, and CRP. The marker may be selected from CRP and CD163. The neurodegenerative disease may be Ataxia Telangiectasia (A-T), the gene is an Ataxia Telangiectasia Mutated gene, and the marker is selected from, CD14, HLA-DR, CD14, CD16, CD4, CD38, CD8, CD38, soluble CD14, soluble CD163, monocyte chemoattractant 1, Osteopontin, C-reactive protein, and interleukin-8. The neurodegenerative disease may be Parkinson's Disease, and the gene may be selected from alpha-synuclein, parkin, leucine-rich repeat kinase 2, PTEN-induced putative kinase 1, protein deglycase, and ATPase 13A2, and combinations thereof. The neurodegenerative disease may be Duchenne's Muscular Dystrophy, and the gene may be dystrophin. The subject may not display a symptom of the neurodegenerative disease before administering the chlorite composition. The subject may not display a physical symptom of the neurodegenerative disease before administering. The subject may not display a behavioral symptom of the neurodegenerative disease before administering. The chlorite composition may be administered by intravenous infusion over a period ranging from about 0.5 to about 4 hours. The chlorite composition may be administered at least once per month for a period of at least a year. The chlorite composition may be administered at least once per week for a period of at least one month. The chlorite composition may be administered in an amount ranging from 0.1 to 10 mg/kg body weight. The amount may be about 1 to about 2 mg/kg body weight.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
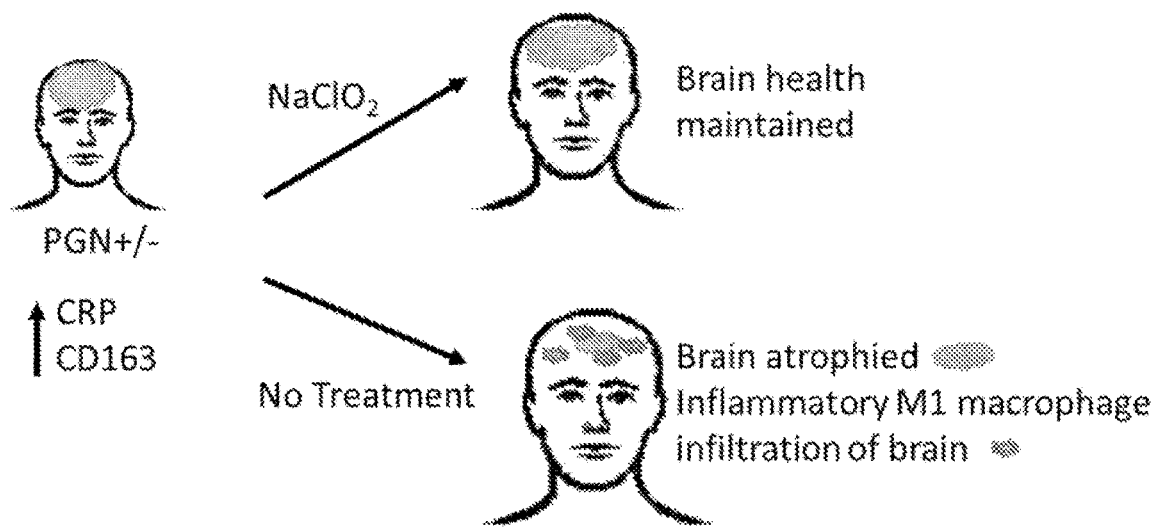
FIG. 1 shows a schematic representation of treating a representative neurodegenerative disease (frontotemporal dementia) with a chlorite composition. The progranulin deficient patient receiving sodium chlorite maintains good brain health. The subject receiving no treatment develops neurodegenerative disease symptoms including an atrophied brain and infiltration of inflammatory M1 type macrophages in the brain.

Evidence for a relationship between neurodegenerative diseases and inflammation has been accumulating over the last several decades, at least. It is generally hypothesized that neurodegenerative disorders can be exacerbated and even initiated by inflammatory conditions. Neurodegenerative conditions are often accompanied by elevated levels of both circulating and cerebral inflammatory markers. However, it is uncertain in most cases whether these inflammatory markers are a cause or effect of the disease. These inflammatory markers may include, but are not limited to tumor necrosis factors (e.g. TNF-alpha), monocyte chemoattractant proteins (e.g. MCP-1), interleukins (e.g. IL-6, IL-12) and chemokine ligands (e.g. CXCL1). These inflammatory proteins may be produced by an array of lymphocytes that include T cells, monocytes and macrophages. Lymphocytes may also include microglial cells and astrocytes, which are considered the 'resident macrophages' of the brain. These inflammatory proteins may interact with surrounding non-lymphocyte cells and non-cellular components of a surrounding tissue, resulting in cellular apoptosis, tissue remodeling and recruitment of additional lymphocytes as an increasingly inflammatory environment establishes itself. Macrophages recruited to these sites may phagocytose dead cells and dead cell components. As macrophages accumulate and become congested at these sites, they may undergo apoptosis as well. Resulting dead cells and components thereof may form plaques or lesions in respective tissues, resulting in tissue dysfunction, and the presentation of symptoms associated with various disorders.

While not wishing to be bound by theory, it is believed that conditions with an inflammatory component, such as various neurodegenerative diseases, may be treated with sodium chlorite. Sodium chlorite may reduce production of one or more inflammatory proteins in monocytes, macrophages, microglia and/or astrocytes. Sodium chlorite may reduce expression of one or more inflammatory proteins in monocytes, macrophages, microglia and/or astrocytes. Sodium chlorite may reduce RNA expression of one or more inflammatory proteins in monocytes, macrophages, microglia and/or astrocytes. Sodium chlorite may reduce maturation of one or more inflammatory proteins in monocytes, macrophages, microglia and/or astrocytes. Reduction of monocyte activities may result in reduced inflammation, removing the driving force behind the neurodegenerative disease. These neurodegenerative diseases may include, but are not limited to A-T, FTD, and Parkinson's disease.

FTD may be exacerbated or driven by inflammation, and therefore reduction of monocytes and/or monocyte activity by sodium chlorite treatment may reduce FTD symptoms. FTD is associated with head trauma and increased cerebrospinal fluid cytokines, notably tumor necrosis factor alpha (TNF-alpha). FTD may be caused by mutations in granulin (GRN) and/or progranulin (PGRN) that are associated with immune and inflammatory disorders. For example, PGRN knockout mice develop inflammatory arthritis. Macrophages from PGRN knockout mice exhibit elevated basal levels of inflammatory cytokines and enhanced production of cytokines in response to inflammatory stimuli. There may also be a greater presence or activity of microglia and astrocytes in the brains of PGRN knockout mice as compared to wildtype mice. Thus, it is hypothesized that FTD may be driven or exacerbated by inflammatory activities of macrophages (including microglia). Therefore, FTD patients may benefit from sodium chlorite, or compositions thereof, that regulate inflammation.

Similarly, other neurodegenerative diseases, including ataxia telangiectasia (A-T), may also be fueled by inflammation and would benefit from sodium chlorite compositions and therapies. As shown in Example 1, lymphocyte CD4 and CD38 reactivity was significantly lower in patients with A-T than in healthy patients, indicating an immune system abnormality in A-T patients.

The term "neurodegenerative" refers to a condition in which brain and nervous systems are affected by the deterioration of neurons. Neurodegenerative conditions include conditions causing problems with movements, conditions affecting memory, conditions related to dementia, or conditions that affect both movement and psychology. For example, see Dyken, P. et al. "Neurodegenerative diseases of infancy and childhood," Ann Neurol., 13: 351-364, (1983).

The term "inflammatory disorder" refers to any change from baseline physiology caused by, or related to, inflammation or inflammatory processes. "Inflammation" can be a pathological process comprising cytological and chemical reactions that occur in affected blood vessels and adjacent tissues in response to injury or abnormal stimulation. Inflammation may arise in response to stimulation or damage from physical, chemical, or biological agents, which may be endogenous or exogenous factors. Examples of endogenous factors include chemical imbalances such as those arising from disease or genetic deficiency, and biological factors, such as the biological responses that lead to repair and healing of injury. Inflammation may be acute or chronic.

The term "monocyte" refers to any lymphocyte or cell that responds to an inflammatory/immune signal and/or produces an inflammatory/immune signal. Macrophages are released from the bone marrow as immature monocytes, circulate in the blood stream, and can eventually migrate into tissues to undergo final differentiation into resident macrophages. When a monocyte enters damaged tissue through the endothelium of a blood vessel (a process known as the leukocyte extravasation), it undergoes a series of changes to become a macrophage. Monocytes and macrophages are attracted to damaged, infected or diseased sites by chemoattractant proteins (chemotaxis), released by macrophages already at the site, an event that is triggered by a range of stimuli including damaged cells, pathogens, cytokines and/or other biomolecules. The terms monocyte and macrophage are used interchangeably herein, unless otherwise specified. Monocytes may be circulating monocytes, traveling through the bloodstream. Monocytes may be resident monocytes, remaining in a tissue. For example, resident macrophages are known as Kupffer cells in liver, alveolar macrophages in the lung, osteoclasts in the bone, and microglia or astrocytes in the brain. Monocytes and macrophages may display phagocytic activity, engulfing and digesting cellular debris and pathogens either as stationary or mobile cells. Monocytes play a role in innate immunity as well as adaptive immunity of vertebrate animals. Monocytes stimulate other lymphocytes or immune cells to respond to pathogens. They can be identified by a number of proteins including CD14, CD11b, F4/80 (mice)/EMR1 (human), Lysozyme M, MAC-1/MAC-3 and CD68 using flow cytometry or immunohistochemical staining (Khazen W, et al. 2005 *FEBS Lett.* 579 (25): 5631-4). At some sites such as the testis, macrophages have been shown to populate the organ through proliferation. Unlike short-lived neutrophils, macrophages survive longer in the body up to a maximum of several months. Thus, while not wishing to be bound by theory, regulation of macrophages in neurodegenerative diseases is one aspect of the invention.

The term "treating" as used herein generally means that the compounds of the invention can be used in humans or animals with at least a tentative diagnosis of childhood genetic neurodegenerative disease such as A-T. In various embodiments, the chlorite compositions of the invention such as sodium chlorite will delay or slow the progression of the disease thereby extending the individual's life span. In various embodiments, the administration of chlorite compositions will improve or relieve symptoms of the disease thus improving quality of life with or without an extension of the individual's life span.

For purposes of the invention, the term "palliative" refers to treatment that is focused on the relief of one or more symptoms of a childhood genetic neurodegenerative disease such as A-T and/or side effects of a therapeutic regimen, but is not curative. For example, palliative treatment encompasses painkillers, anti-nausea medications and anti-sickness drugs.

As used herein, ranges and amounts can be expressed as "about" a particular value or range. About also includes the exact amount. For example, "about 5 µL" means "about 5 µL" and also "5 µL." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value. A p-value of less than 0.05 is considered statistically significant.

The symptoms and diagnostic criteria for medical and psychiatric conditions are known in the art and can be found in such texts as The Pathologic Basis of Disease, Vinay Kumar, Nelson Fausto, Abul K. Abbas eds. (2004); DSM-IV-TR (American Psychiatric Association: Diagnostic and Statistical Manual of Mental Disorders, Fourth Edition, Text Revision, Washington D.C., American Psychiatric Association (2000); and The Merck Manual of Diagnosis and Therapy, 17th Edition (1999).

Methods

Provided herein are methods of treating neurodegenerative conditions with chlorite-containing formulations. The formulations may contain sodium chlorite, calcium chlorite, or a combination thereof. The chlorite formulations disclosed herein may be particularly useful for neurodegenerative diseases with an inflammatory component. Examples of neurodegenerative diseases with an inflammatory component include Alzheimer's disease (AD), Pick's disease, Lewy body dementia, Huntington's disease, Amyotrophic Lateral Sclerosis, Parkinson's disease, Ataxia Telangiectasia, and Frontotemporal Dementia (FTD). The chlorite formulation may reduce the presence or production of an inflammatory component that contributes to the neurodegenerative disease. In some cases, this inflammatory component may also be an inflammatory marker of the neurodegenerative disease. For example, the inflammatory marker may be circulating C-reactive protein or CD163 in a patient with FTD. Plasma levels of CRP or CD163 in the FTD patient may be reduced by treatment with a chlorite formulation.

The methods of treating patients include treating those subjects diagnosed with the neurodegenerative disease as well as those subjects that may not be clinically diagnosed, but display one or more symptoms of a neurodegenerative disease. The methods disclosed herein also include methods of preventing, delaying or reducing the symptoms of the neurodegenerative disease. Preventing, delaying or reducing the symptoms may be achieved by determining if the subject has a genetic mutation predisposing the subject to the neurodegenerative disease, and treating the subject with sodium chlorite before onset of symptoms. Thus, the methods comprise treating a subject with a chlorite formulation when they are suspected of developing a neurodegenerative disease. The subject may be suspected of developing a neurodegenerative disease when they have a genetic mutation known to present a risk to the subject of developing the neurodegenerative disease. The subject suspected of developing a neurodegenerative disease may also display a marker of the neurodegenerative disease. The marker may be an inflammatory marker, such as an inflammatory marker in the blood of the patient or the presence of ubiquitinated neuronal intranuclear inclusions in the brain. In some cases, the methods comprise detecting or quantifying the marker in a sample (e.g., blood or urine) from the subject before onset of symptoms.

Provided herein are methods of treating, preventing, delaying or reducing at least one symptom of a neurodegenerative disease disclosed herein with a chlorite composition disclosed herein. The symptom of the neurodegenerative disease may be a behavioral symptom. The behavioral symptom may be selected from, but is not limited to, speech problems, speech disorders, language disorders, loss of empathy, repetitive compulsive behavior, increasingly inappropriate actions, loss of empathy and other interpersonal skills, lack of judgment and inhibition, apathy, repetitive compulsive behavior, emotional blunting, loss of insight, changes in eating habits, predominantly overeating, lack of awareness of thinking, and behavioral changes. The symptom of the neurodegenerative disease may be a physical symptom. The physical symptom may be selected from, but is not limited to, tremor, bradykinesia, rigidity, postural instability, freezing, micrographia, mask-like expression, unwanted accelerations, stooped posture, dystonia, impaired fine motor dexterity, impaired gross motor coordination, akathisia, muscle spasms, difficulty swallowing, loss of sense of smell, REM behavior disorder, mood disorders, orthostatic hypotension, and sleep disturbances, poor coordination, muscle weakness, progressive muscle weakness, muscle wasting, progressive muscle wasting, hyperreflexia, spasticity, and respiratory failure.

Provided herein are neurodegenerative diseases characterized by at least one marker in a sample of the subject. Further provided herein are methods of administering a chlorite composition to a subject with a neurodegenerative disease, wherein the chlorite composition alters the amount of marker present in the sample of the subject. The methods disclosed herein may comprise collecting the sample. The sample may be blood, plasma, serum, cerebrospinal fluid, urine, lymphatic fluid, saliva or a combination thereof. Alternatively, the sample may be a brain image. The brain image may be collected with known imaging methods such as, by way of non-limiting example, PET-SCAN or MRI. The marker may be an inflammatory marker. The marker may be an immune system functional marker. The inflammatory marker is generally a peptide or protein that is cell-free (e.g., secreted by or release from a cell), and an immune system functional marker is generally a peptide or protein expressed on the surface of a cell. By way of non-limiting example, inflammatory markers include interleukins, tumor necrosis factors, chemokines, cytokines, metalloproteases, immunoglobulins, and pathogen fragments or products (e.g., pathogen-associated molecular patterns (PAMPs), lipopolysaccharide, lipid A). By way of non-limiting example, immune system functional markers include glycoproteins, checkpoint inhibitors (e.g., PD-L1, PD-1), cluster of differentiation proteins (e.g., CD3, CD8, CD10, CD19, CD68, CD276, CD278), interleukin receptors, TNF receptors (e.g., OX40), and proteins that are critical for metabolism or development of immune cells (e.g., IDO-1, FoxP3). The marker may be a protein aggregate marker. Non-limiting examples of a protein aggregate marker are tau protein, amyloid beta, ubiquitin, superoxide dismutase 1, RNA-binding protein FUS, and TAR DNA binding protein (TDP-43, or TARDBP).

Provided herein are neurodegenerative diseases characterized by an elevated level of at least one marker in a sample of the subject. The elevated level of the marker may be at least about 20% higher than the level of the marker of the control subject. The elevated level of the marker may be at least about 30% higher than the level of the marker of the control subject. The elevated level of the marker may be at least about 40% higher than the level of the marker of the control subject. The elevated level of the marker may be at least about 50% higher than the level of the marker of the control subject. The elevated level of the marker may be at least 20% higher than the level of the marker of the control subject. The elevated level of the marker may be at least 30% higher than the level of the marker of the control subject. The elevated level of the marker may be at least 40% higher than the level of the marker of the control subject. The elevated level of the marker may be at least 50% higher than the level of the marker of the control subject.

Provided herein are methods of detecting or quantifying a marker in a subject with a neurodegenerative disease, or suspected of having a neurodegenerative disease, and comparing the presence or quantity of the marker to that of a control subject. The control subject may be a subject that does not have the neurodegenerative disease. The control subject may be a subject that does not display a symptom of the neurodegenerative disease. The control subject may be a subject that is not clinically diagnosed or informally diagnosed with a disease or condition of any kind (e.g., a healthy subject). The control subject may be a subject that does not present a symptom of any disease or condition of any kind (e.g., a healthy subject).

Neurodegenerative Diseases

In one aspect are provided methods of treatment of neurodegenerative diseases with a chlorite composition. In a preferred embodiment, the chlorite composition is a pharmaceutically acceptable salt of chlorite. For example, in various embodiments, the pharmaceutically acceptable salt is sodium chlorite.

In various embodiments, the neurodegenerative disease is a childhood neurodegenerative disease, also referred to herein as a genetic neurodegenerative disease or a childhood genetic neurodegenerative disease. The childhood neurodegenerative disease may be a neurodegenerative disease wherein the symptoms of the neurodegenerative disease begin in childhood. Methods provided herein for treating a subject having a childhood neurodegenerative disease may comprise treating a subject that is less than 18 years old. In some cases, the subject is less than 16 years old. In some cases, the subject is not older than 13 years old. In some cases, the subject is not older than 12 years old. In some cases, the subject is not older than 10 years old. In various embodiments, the neurodegenerative disease is a childhood genetic neurodegenerative disease which is an inflammatory disorder. In some embodiments, the neurodegenerative disease has an inflammatory component.

In various embodiments, the neurodegenerative disease, any of which can be a childhood neurodegenerative disease, is selected from the group consisting of the following:

Achondroplasia and variants (DE)
Acute cerebellar ataxia (SE)
Acute delayed measles encephalitis (Lyon) (PE)
Acute disseminated encephalomyelitis (LE)
Acute hemorrhagic necrotizing leukoencephalitis (LE)
Adrenoleukodystrophy and variants (LE)
Adrenomyeloneuropathy (LE)
Aicardi syndrome of flexor spasms, callosal agenesis, and optic hypoplasia (DE)
Albinism with degenerative features and variants (DE)
Albright hereditary osteodystrophy (CE)
Alcoholic encephalopathy (DE)
Alexander fibrinoid leukodystrophy and variants (LE)
Alpers poliodystrophy (PE)
Alpha-aminoadipic aciduria (DE)
Alpha-ketoadipic aciduria (DE)
Alpha-methyl-beta-hydroxybutyric aciduria (DE)
Amyotrophic Lateral Sclerosis (ALS)
Angleman happy puppet syndrome (DE)

Arginemia (DE)
Arginosuccinic aciduria (DE)
Aspartylglucosaminuria (DE)
Ataxia telangiectasia (CE)
Autism with polioencephalopathy (PE)
Balo encephalitis periaxialis concentrica (LE)
Bassen-Komzweig disease (SE)
Behget syndrome (CE)
Behr optic-spinocerebellar degeneration (SE)
Biemond posterior column ataxia (SE)
Bloch-Sulzberger disease (incontinentia pigmenti) (DE)
Blue diaper syndrome (DE)
Canavan spongiform leukodystrophy (LE)
Carbamyl phosphate synthetase deficiency (DE)
Carbon monoxide encephalopathy (CE)
Camitine deficiency (DE)
Camosinemia (hypercamosinemia) (DE)
Central pontine myelinolysis (LE)
Cerebrohepatorenal syndrome (Zellweger disease) (DE)
Cerebrotendinous xanthomatosis (DE)
Charcot-Marie-Tooth disease and variants (SE)
Chediak-Higashi disease (DE)
Chronic congenital "torch" encephalopathies (PE)
Chronic congenital toxoplasmosis with late degeneration (PE)
Chronic cytomegalovirus infection (PE)
Chronic encephalopathy with liver insufficiency (CE)
Chronic encephalopathy with pulmonary insufficiency (DE)
Chronic hereditary spinocerebellar degeneration (SE)
Chronic lymphocytic meningitis (DE)
Chronic manganese encephalopathy (CE)
Chronic "torch" encephalopathy with myoclonia (CE)
Chronic toxic encephalopathies (PE)
Citrullinemia (DE)
Cockayne syndrome (LE)
Cogan syndrome of interstitial keratitis, vertigo, and deafness (SE)
Collagen-vascular syndromes with encephalopathy (DE)
Congenital demyelinating encephalopathy (Mackay) (DE)
Congenital indifference to pain (CE)
Congenital myophosphorylase deficiency (SE)
Conradi chondrodystrophia calcificans congenita (DE)
Craniosynostosis (DE)
Crigler-Najjar kernicterus and variants (CE)
Cutaneous meningeal melanosis (DE)
Cystathioninuria (DE)
Cystinosis (DE)
Cystinuria (DE)
Cytosol tyrosine aminotransferase deficiency (DE)
Delange-Brachmann syndrome (LE)
Delange congenital muscle hypertrophy and extrapyramidal disturbances (CE)
Devic neuromyelitis optica (LE)
Diabetes mellitus encephalopathy (DE)
Disseminated encephalomalacia with cavity formation (Stevenson, Ford) (LE)
Disseminated sarcoid leukoencephalopathy (LE)
Double athetosis of Vogt (status demyelinasatus) (CE)
Down syndrome with dementia (DE)
Dystonia musculorum deformans and variants (CE)
Fabry angiokeratoma corporis diffusum (DE)
Fahr disease (CE)
Familial calcifying polioencephalopathy (Geylin, Penfield) (PE)
Familial deteriorating extrapyramidal syndrome (CE)
Familial hypertrophic interstitial neuritis (Dejerine-Sottas) (SE)
Familial hypertrophic paraprotein polyneuritis (Gibberd, Gabrilescu) (SE)
Familial methemoglobinemia (DE)
Familial multilocular encephalomalacia (Crome, Williams) (LE)
Familial olivopontocerebellar degeneration and variants (Konigsmark, Weiner) (SE)
Familial paroxysmal chorea-athetosis-dystonia (CE)
Familial protein intolerance (DE)
Familial striatal degeneration (CE)
Familial Werdnig-Hoffmann progressive spinal atrophy (SE)
Farber lipogranulomatosis (LE)
Fazio-Londe familial amyotrophic lateral sclerosis (SE)
Fibrous dysplasia of the skull with encephalopathy (DE)
Focal dermal hypoplasia (Gorlin) (DE)
Ford "312" basal ganglion syndromes (CE)
Ford "312" spinocerebellar syndromes (SE)
Friedreich ataxia (SE)
Frontotemporal dementia
Frontotemporal lobar degeneration
Fructose intolerance and variants (DE)
Galactosemia and variants (DE)
GM, gangliosidoses and variants (PE)
GM2 gangliosidoses and variants (Tay-Sachs disease) (PE)
Gaucher disease and variants (DE)
Genetic cretinism (DE)
Giant axonal neuropathy (SE)
Glutamate dehydrogenase deficiency (spinocerebellar degeneration) (SE)
Glutamyl cysteine synthetase deficiency (DE)
Glutaric aciduria and variants (DE)
Glutathionemia (DE)
Glycerol kinase deficiency (Guggenheim) (DE)
Glycopeptidosis (DE)
Haas sex-linked disease with copper metabolism defect (CE)
Hallervorden-Spatz disease (CE)
Harada syndrome of choroiditis, vitiligo, and deafness (SE)
Hartnup disease (SE)
Heller dementia (PE)
Hematosidosis (anabolic GM3 gangliosidosis) (PE)
Hemoglobinopathy encephalopathy (DE)
Hemophilic encephalopathy and variants (DE)
Hereditary bulbar atrophy (Fazio-Londe) (SE)
Hereditary cerebellar ataxia (Menzel, Holmes) (SE)
Hereditary cerebellar ataxia with mental deficiency (Norman, Jervis) (SE)
Hereditary hemorrhagic telangiectasia (DE)
Hereditary macular dystrophies with encephalopathy (DE)
Hereditary motor-sensory neuropathy (England, Denny-Brown) (SE)
Hereditary myoclonic encephalopathy (CE)
Hereditary poliodystrophy (PE)
Hereditary sensory neuropathy (Hicks, Denny-Brown) (SE)
Hereditary spastic paraplegia (SE)
Heredofamilial brachial plexus neuritis (Taylor) (SE)
Herpes zoster with myelopathy (SE)
Hippel-Lindau hemangioblastosis (DE)
Histidinemia and variants (DE)
Histiocytosis and variants (DE)

Holmes-Logan infantile CNS degeneration (CE)
Holocarboxylase deficiency (Biotin) (DE)
Homocamosinuria (DE)
Homocystinuria and variants (DE)
Huntington disease (CE)
Hunt juvenile paralysis agitans (familial) (CE)
Hunt juvenile paralysis agitans (sporadic) (CE)
Hyperammonemias with diffuse encephalopathy (DE)
Hyper-B-alanemia (DE)
Hyperendorphin syndrome of necrotizing encephalopathy (Brandt) (CE)
Hyperglycinemia (nonketotic) (DE)
Hyperglycinemia with valproate therapy (DE)
Hyperlysinemia (DE)
Hypermethionemia (DE)
Hyperphenylalanemia and variants (DE)
Hyperpipecolatemia (DE)
Hyperprolinemia and variants (DE)
Hypertryptophanemia (DE)
Hypervalinemia (DE)
Hypophosphatasia (DE)
Hypoxic degenerative encephalopathy with infantile spasms (DE)
Hypoxic degenerative polioencephalopathy (CE)
Hypoxic degenerative polioencephalopathy with infantile spasms (PE)
Idiopathic degenerative encephalopathy (DE)
Idiopathic dementia/autism (PE)
Idiopathic dementia with polioencephalopathy (PE)
Idiopathic hypoparathyroidism (DE)
Idiopathic sporadic polioencephalopathy (PE)
Idiopathic subcortical degeneration (CE)
Immunodeficiency syndromes with encephalopathy (genetic) (DE)
Immunodeficiency syndromes with encephalopathy (sporadic) (DE)
Infantile neuronal degeneration (Steiman, Radermacher) (CE)
Infantile polymyoclonia (CE)
Isovaleric acidemia (DE)
Jervis cholesterol deposits with chronic encephalopathy (DE)
Joseph disease, type I (SE)
Juvenile Creutzfeldt-Jakob disease (CE)
Juvenile disseminated sclerosis (LE)
Juvenile dystonic lipidosis (CE)
Juvenile neuroaxonal dystrophy (CE)
Keratosis follicularis (DE)
Kemicterus (CE)
Krabbe globoid cell leukodystrophy and variants (LE)
Kuru (CE)
Lactic acidemia (DE)
Lactosyl-ceramidosis (PE)
Laurence-Moon-Biedl syndrome (DE)
Lead encephalopathy, chronic (DE)
Leber hereditary optic neuropathy (DE)
Leigh subacute necrotizing encephalomyelitis and variants (CE)
Lennox-Gastaut syndrome (PE)
Leprechaunism (Donohue) (DE)
Leprosy dementia (DE)
Lesch-Nyhan disease (CE)
Lethargic encephalitis of Economo (CE)
Letterer-Siwe histiocytosis (DE)
Leukoencephalopathy with ragged red fibers (LE)
Linear sebaceous nevus of Jadassohn with encephalopathy (DE)
Lipodystrophic muscular hypertrophy with encephalopathy (DE)
Lowe oculocerebrorenal syndrome (PE)
Lysine intolerance (DE)
Malabsorption syndromes with encephalopathy (DE)
Malignant papulosis (DE)
Maple syrup urine disease and variants (LE)
Marfan disease (DE)
Marinesco-Sjogren-Garland syndrome (SE)
Menkes trichopoliodystrophy (PE)
Metabolic poliodystrophy (PE)
Metachromatic leukodystrophy and variants (LE)
Methylmalonic acidemia and variants (DE)
Metrizamide encephalopathy with asterixis (CE)
Mollaret recurrent meningitis (SE)
Mucolipidoses and variants (PE)
Mucopolysaccharidoses and variants (PE)
Mucosulfatidosis (DE)
Multiple cerebroretinal arteriovenous malformations (Wybom-Mason) (CE)
Multiple lipomatosis with chronic encephalopathy (DE)
Multisystem neuronal degeneration (Dyck) (DE)
Myoclonic encephalopathy with progressive cranial nerve palsies (Dyken) (CE)
Myoclonic-plus syndromes (Dyken) (CE)
Neonatal endotoxin encephalopathy (DE)
Neurofibromatosis (DE)
Neuroichthyosis with dementia (DE)
Neuronal ceroid lipofuscinoses and variants (PE)
Nevus unis lateris (DE)
Niemann-Pick sphingomyelinosis and variants (PE)
Norman-Wood congenital amaurotic familial idiocy (PE)
Nutritional deficiency syndromes with encephalopathy (DE)
Oasthouse urine disease (DE)
Oligosaccharidoses and variants (PE)
Ophthalmoplegia-plus syndromes (CE)
Opsoclonic meningoencephalitis (CE)
Opticocochlodentatic degeneration (DE)
Organic mercury cerebellar degeneration (SE)
Omithine carbamylase deficiency (DE)
Omithinemia (HHH syndrome) (DE)
Orthochromatic leukodystrophy and variants (LE)
Osteopetrosis (DE)
5-Oxoprolinemia (glutathionine synthetase deficiency) (DE)
Parkinson's Disease
Parry-Romberg hemifacial atrophy with encephalopathy (DE)
Pelizaeus-Merzbacher disease and variants (LE)
Peroxidase deficiency (Boehme) (CE)
Phenylketonuria and variants (LE)
Phenytoin cerebellar degeneration (SE)
Phenytoin dementia/degeneration (PE)
Pleonosteosis of Leri (DE)
Poikiloderma congenitale (DE)
Pompe disease (SE)
Porphyria and variants (PE)
Postpertussis encephalopathy (PE)
Postvaccinal encephalopathy (PE)
Primary gliosis of the brain (DE)
Progeria (Hutchinson-Gilford) (DE)
Progeria (Werner) (DE)
Progressive dementia with photosensitivity (Kloepfer) (LE)
Progressive hereditary diaphyseal dysplasia (Engelmann) (DE)

Progressive hereditary nerve deafness (SE)
Progressive pallidal degeneration (Winkelman) (CE)
Progressive rubella panencephalitis (LE)
Proprionic acidemia and variants (DE)
Pyruvate carboxylase deficiency (CE)
Pyruvate dehydrogenase complex deficiency (CE)
Radiation-induced encephalopathy (DE)
Ragged-red mitochondrial disease (Kearns-Sayre) (CE)
Ramsay-Hunt dentatorubral atrophy (CE)
Refsum disease (heredopathia atactica polyneuritiformis) (SE)
Rendu-Osler-Weber hemangiomatosis (DE)
Riley-Day dysautonomia (CE)
Roussy-Levy disease (SE)
Rubinstein-Taybi syndrome (DE)
Saccharopinuria (DE)
Salta disease (PE)
Sarcosinemia (DE)
Schilder encephalitis periaxialis diffusa (LE)
Segawa hereditary progressive dystonia (diumal) (CE)
Seitelberger infantile neuroaxonal dystrophy (CE)
Sex-linked ataxia with myoclonia and extrapyramidal signs (CE)
Sex-linked leukodystrophy (LE)
Sialidoses and variants (PE)
Sotos cerebral gigantism (DE)
Spongiform polioencephalopathies and variants (PE)
Sporadic cretinism (DE)
Sporadic juvenile amyotrophic lateral sclerosis (SE)
Sporadic myoclonic encephalopathy (CE)
Sporadic olivopontocerebellar degeneration (Dejerine-Thomas) (SE)
Sporadic optic neuritis, retrobulbar neuritis (LE)
Sporadic primary lateral sclerosis (SE)
Sporadic progressive thalamic atrophy (CE)
Sporadic spongiform encephalopathies with myoclonus (CE)
Status marmoratus (CE)
Sturge-Weber disease (DE)
Subacute myelo-optic neuropathy (acrodermatitis enteropathica) (DE)
Subacute sclerosing panencephalitis and variants (LE)
Subthalamic nuclear degeneration (Malmud, Denny) (CE)
Sugarman-Reed craniofacial leukoderma (DE)
Sulfituria (sulfate oxidase) (DE)
Supranuclear ophthalmoplegia (hereditary) (CE)
Sydenham chorea (CE)
Syndrome of the sea-blue histiocyte (SE)
Syringomyelia (familial) (SE)
Tourette syndrome (CE)
Transitional diffuse sclerosis (LE)
Triose phosphate isomerase deficiency (CE)
Tuberous sclerosis (DE)
Tyrosinemia (DE)
Unverricht-Lundborg-Lafora disease (CE)
Vogt-Koyanagi syndrome (SE)
Waardenburg syndrome (DE)
Wadia-Swami spinocerebellar degeneration (SE)
Weill-Marchesani syndrome (DE)
Welander-Kugelberg-Wohlfart juvenile spinal atrophy (SE)
West disease (idiopathic infantile spasms with degeneration) (PE)
West disease (non-genetic diffuse encephalopathy) (DE)
Wilson hepatolenticular degeneration and variants (CE)
Wolman encephalopathy (LE)
Xeroderma pigmentosum and variants (SE)

In various embodiments, the disease is a well-known neurodegenerative disease. In various embodiments the neurodegenerative disease is Alzheimer's disease, Pick's disease, Lewy body dementia, Huntington's disease or Parkinson's disease.

Encephalopathies

According to the above listing, CE indicates corencephalopathies; DE indicates diffuse encephalopathies; LE indicates leukoencephalopathies; PE indicates polioencephalopathies; and SE indicates spinocerebellopathies.

In various embodiments, the neurodegenerative disease is a corencephalopathy. In various embodiments, the neurodegenerative disease is a corencephalopathy which is also an inflammatory disorder.

Ataxia Telangiectasia

In various embodiments, the disease is Ataxia Telangiectasia (A-T). Symptoms of A-T may include, but are not limited to, ataxia (difficulty with control of movement); oculomotor apraxia (difficulty with coordination of head and eye movement when shifting gaze from one place to the next), involuntary movements, telangiectasia (dilated blood vessels) over the white (sclera) of the eyes, making them appear bloodshot; problems with infections, especially of the arse, sinuses and lungs; delayed onset pubertal development and very early menopause; slowed rate of growth (weight and/or height), dysarthria (slurred, slow or distorted speech sounds); diabetes in adolescence or later; and premature changes in hair and skin. In various embodiments, the chlorite compound is used to reduce or treat symptoms of A-T.

Immune abnormalities are important features of pathophysiology and the treatment of neurodegenerative diseases including A-T. In various embodiments the patient with A-T has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with A-T by administration of a chlorite compound. In various embodiments, the chlorite compound reduces or corrects these immune abnormalities thereby reducing or treating the symptoms of A-T.

Frontotemporal Dementia (FTD)

In various embodiments, the disease is frontotemporal dementia (FTD), sometimes referred to in the art as frontotemporal degeneration, frontotemporal lobar degeneration (FTLD), or behavioral variant FTD, all of which can be used interchangeably. Symptoms of FTD may include, but are not limited to, increasingly inappropriate actions, loss of empathy and other interpersonal skills, lack of judgment and inhibition, apathy, repetitive compulsive behavior, emotional blunting, loss of insight, changes in eating habits, predominantly overeating, lack of awareness of thinking or behavioral changes, tremor, rigidity, muscle spasms, poor coordination, difficulty swallowing, muscle weakness, speech disorders, and language disorders. In various embodiments, the chlorite compound is used to reduce or treat symptoms of FTD.

Immune abnormalities are important features of pathophysiology and targets of treatment for neurodegenerative diseases including FTD. In various embodiments, the subject with FTD has abnormal levels of circulating (e.g., plasma) proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with FTD by administration of a chlorite compound. In various embodiments, the chlorite compound reduces or corrects these immune abnormalities thereby reducing or treating the symptoms of FTD.

In some embodiments, soluble CD163 (sCD163) expression is elevated in the subject with FTD. In some embodiments, CRP expression is elevated in the subject with FTD. In some embodiments, CRP expression (e.g., high wr-CRP "carrier" plasma) is monitored, tracked or measured in response to chlorite therapy. In some embodiments, treatment with chlorite modifies monocyte expression of CD16 and HLA-DR.

In some embodiments, the subject with FTD carries a mutation in a gene selected from superoxide dismutase 1 gene (SOD1), alsin (ALS2), probably helicase senataxin (SETX), spatacsin (SPG11), fused in sarcoma gene (FUS), vesicle-associated membrane protein-associated protein B/C (VAPB), angiogenin (ANG), transactive response DNA binding protein 43 kDa (TDP-43, TARDBP), polyphosphoinositide phosphatase (FIG. 4), optineurin (OPTN), ataxin-2 (ATXN2), valosin containing protein (VCP), ubiquilin-2 (UBQLN2), sigma-1 receptor (SIGMAR1), charged multivesicular body protein 2B (CHMP2B), profiling-1 (PFN1), receptor tyrosine-protein kinase erbB-4 (ERBB4), heterogeneous nuclear ribonucleoprotein A1 (HNRNPAI), matrin-3 (MATR3), tubulin alpha-4A chain (TUBA4A), C9orf72, coiled-coil-helix-coiled-coil-helix domain containing 10 (CHCHD10), sequestosome-1 (SQSTM1), serine/threonine-protein kinase (TBK1), c9orf72, microtubule associated protein tau (MAPT), progranulin (PGN, GRN), and combinations thereof. In some embodiments, the subject with FTD carries a mutation in a c9orf72 gene. In some embodiments, the subject with FTD carries a mutation in a MAPT gene. In some embodiments, the subject with FTD carries a mutation in a TARDBP gene. In some embodiments, the subject with FTD carries a mutation in a VCP gene. In some embodiments, the subject with FTD carries a mutation in a CHMP2B gene. In some embodiments, the subject with FTD carries a mutation in a SOD1 gene. In some embodiments, the subject with FTD carries a mutation in a FUS gene. In some embodiments, the subject with FTD carries a mutation in a PGN gene.

In some embodiments, the subject with FTD carries a mutation in a progranulin (PGN) gene. Progranulin is also sometimes designated with the acronym GRN, by those in the field. In some embodiments, the subject with FTD carries an autosomal mutation in the progranulin gene. In some embodiments, the subject with FTD carries a sporadic mutation in the progranulin gene. In some embodiments, the subject with FTD carries a mutation in the progranulin gene selected from br272fs(g.1977_1980delCACT, Cys157fs (g.1283_1289delCTGCTGT, and a combination thereof. In some embodiments, the subject with FTD that carries a mutation in PGN, has an elevated level of a cytokine, a chemokine, or a related receptor in their cerebrospinal fluid or serum, relative to a subject without FTD or without an inflammatory condition. In some embodiments, the chemokine is monocyte chemoattractant protein-1 (MCP-1). In some embodiments, the cytokine is interferon-gamma inducible protein-10 (IP-10). In some embodiments, the subject with FTD that carries a mutation in PGN, has a reduced level of neuroprotective factor in their cerebrospinal fluid. The neuroprotective factor may be interleukin-15 (IL-15) or RANTES. One third of PGN mutation "carriers" have abnormal levels of wr-CRP on the order of that observed in FTD patients. These patients would be predicted to progress to symptomatic FTD at a faster rate than "carriers" with normal levels of wr-CRP. As such, the methods disclosed herein provide for study of: FTD prevention, identification of differentiation and gene expression profiles of PGN mutant carriers during the "switch" from asymptomatic to symptomatic FTD. The methods may disclose measuring and/or monitoring levels of CRP in the subject. The methods disclosed herein provide for an identification of a "trigger" that drives the conversion of "genetic predilection" of genetic forms of neurodegenerative disease to frank symptomatic disease. By comparing FTD, with high wr-CRP vs low wr-CRP carriers this conversion step may be defined.

Further disclosed herein are methods comprising an assay for monocyte gene/protein expression and/or activity. In some embodiments, the methods comprise obtaining a monocyte or macrophage from the subject. In some embodiments, the methods comprise characterizing a monocyte or macrophage phenotype from the subject. In some embodiments, the methods may comprise identifying a therapeutic agent that regulates macrophage activity, thereby delaying, arresting, or reversing FTD. In some embodiments, a chlorite composition may prevent, delay, arrest, or reverse the conversion of asymptomatic FTD to symptomatic FTD in genetic carriers of abnormal genes associated with neurodegenerative diseases described herein.

In some embodiments, methods disclosed herein comprise measuring a level of an LPS binding protein (LBP) in the plasma of the subject. The elevation of LBP in carriers in the asymptomatic group that are in the process of converting to FTD may have elevation of LPS in their plasma. In some embodiments, the methods comprise identifying a specific species of bacteria responsible for microbial translocation and LPS causing the elevated LBP. In some embodiments, the methods comprise administering a probiotic treatment directed to this bacterial species. Thus, the methods disclosed herein may prevent the conversion of carrier state to FTD disease before any symptom appears.

There is some uncertainty in the field about whether FTD and ALS are distinct diseases or if ALS is a more progressed form of ALS. However, FTD is observed in subjects that never develop ALS, and, conversely, ALS is observed in subjects that never had FTD. There may be subpopulations within a population experiencing both conditions or either condition. One subpopulation may have FTD that never progresses to ALS. Another subpopulation may have ALS without previously displaying symptoms of FTD. An additional subpopulation may have FTD followed by ALS. Another population may experience symptoms of FTD and ALS concurrently. The difference between a subject having ALS that comes on quickly without the subject ever experiencing FTD and a subject that has FTD, but never develops ALS may be due to genetic factors and environmental factors, such as inflammation. For instance, a subject who has a genetic mutation predisposing them to FTD and/or ALS may only present with FTD, and not ALS, if they maintain a low inflammatory state (e.g., well-managed infections, no other inflammatory conditions). In other instances, the subject who has a genetic mutation predisposing them to FTD and/or ALS may progress from FTD to ALS, or may experience ALS only, if the subject experiences inflammation. The inflammation may be genetic. The inflammation may be environmental. Although chlorite formulations may be useful for treating ALS, it may be useful only for a sub-population of subjects with FTD. Chlorite formulations may be useful for treating FTD when FTD is associated with inflammation or elevated levels of inflammatory markers, as described herein.

Regardless of whether FTD or ALS represent a spectrum of a condition or they are their own conditions, FTD and ALS may be separately diagnosed and characterized by different symptoms. The most commonly used diagnostic criteria for FTD is the Neary criteria, which is focused on the behavioral symptoms, expressive language disorders, semantic dementia and progressive non fluent aphasia. The most commonly used diagnostic criteria for ALS is the El Escorial revised criteria, with the use of clinical and electrophysiological/neuropathological examination to assess lower motor neuron degeneration, upper motor neuron degeneration and spreading of the neurodegeneration from one brain region to another. ALS diagnosis may be subcategorized into pure ALS, ALS with cognitive impairment, ALS with behavioral impairment, and ALS with signs of FTD based on the Neary criteria. Both FTD and ALS may be characterized by ubiquitin-positive neuronal inclusions. FTD and ALS may additionally, or alternatively, be characterized by TDP-43 aggregates.

The subject may have FTD. FTD is generally characterized by atrophy of the frontal and temporal lobes. The methods disclosed herein may comprise further assessing (e.g., neuroimaging) atrophy of the frontal and/or temporal lobes of the brain of the subject. The subject may have FTD associated with ubiquitin pathology. The subject may have FTD associated with tau pathology. Tau pathology may be associated with mutations, either gain-of-function or loss-of-function, in the microtubule associated protein TAU gene (MAPT). Tau pathology may not be associated with mutations in the microtubule associated protein TAU gene (MAPT). The subject may have FTD associated with tau pathology and ubiquitin pathology.

The subject may have ALS. The subject with ALS may have some characteristics common to FTD, such as, by way of non-limiting example, subclinical frontal dysfunction, language impairment and progressive aphasia. ALS may produce symptoms that may not be observed in FTD patients, such as, by way of non-limiting example, hyperreflexia, spasticity, progressive muscle weakness, progressive muscle wasting and respiratory failure. In some embodiments, the subject with ALS carries a mutation in a gene selected from SOD1, ALS2, SETX, SPG11, FUS, VAPB, ANG, TARDBP, FIG4, OPTN, ATXN2, VCP, UBQLN2, SIGMAR1, CHMP2B, PFN1, ERBB4, HNRNPAI, MATR3, TUBA4A, C9orf72, CHCHD10, SQSTM1, and TBK1, and combinations thereof.

Alzheimer's Disease

In various embodiments, the disease is Alzheimer's disease. Symptoms of Alzheimer's disease include, but are not limited to, memory loss, dementia, and slow decline in memory, thinking and reasoning skills. In various embodiments, the chlorite compound is used to reduce or treat symptoms of Alzheimer's disease.

Immune abnormalities are important features of pathophysiology and the treatment of neurodegenerative diseases including Alzheimer's disease. In various embodiments the patient with Alzheimer's disease has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with Alzheimer's disease by administration of a chlorite compound. In various embodiments, the chlorite compound reduces or corrects these immune abnormalities thereby reducing or treating the symptoms of Alzheimer's disease.

Parkinson's Disease

In various embodiments, the disease is Parkinson's disease. Symptoms of Parkinson's disease include, but are not limited to, resting tremors, bradykinesia, rigidity, postural instability, freezing, micrographia, mask-like expression, unwanted accelerations, stooped posture, dystonia, impaired fine motor dexterity, impaired gross motor coordination, akathisia, speech problems, difficulty swallowing, loss of sense of smell, REM behavior disorder, mood disorders, orthostatic hypotension, and sleep disturbances. In various embodiments, the chlorite compound is used to reduce or treat symptoms of Parkinson's disease.

Immune abnormalities are important features of pathophysiology and the treatment of neurodegenerative diseases including Parkinson's disease. In various embodiments the patient with Parkinson's disease has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with Parkinson's disease by administration of a chlorite compound. In various embodiments, the chlorite compound reduces or corrects these immune abnormalities thereby reducing or treating the symptoms of Parkinson's disease.

Treatment of Parkinson's Disease with Chlorite Composition

Chlorite composition administration and survival studies have been done in G93A SOD-1 mt. mouse model of ALS. In this model, the SOD-1 mutant mice begin developing degeneration of neurologic function starting at approximately 70 days of age. The mice were dosed with chlorite composition at 2 mg/kg intravenously every three weeks with neuroscore and survival information being collected weekly. Chlorite treated animals survived almost three weeks longer than sham treated animals and neurologic degeneration was also delayed by a similar time. The SOD-1 model of ALS involves ongoing migration of activated monocytes from blood into spinal cord suggesting that chlorite composition could have had its effect on survival by modulating peripheral blood monocytic activation levels without affecting the CNS directly.

Overexpression of hα-synuclein in the substantia nigra of mice leads to microglia activation by 2 months and loss of dopaminergic neurons and their striatal projections by 6 months. Immune activation and MHC-II expression is required for robust nigral degeneration in the rAAV2/5-hα-synuclein mouse model of Parkinson's disease. This model is ideal for testing the ability of chlorite composition to switch the inflammatory phenotype of microglia/monocytes to a more phagocytic one that can clear the increased hα-synuclein and exert protect nigral neurons from its toxicity. Administration of chlorite to patients with chronic inflammatory diseases or non-healing wounds results in reversal of inflammation and resolution of tissue damage associated with the disease being treated. There are common features shared by most neurodegenerative diseases that result in accumulation of abnormal proteins/abnormally folded proteins that subsequently incite secondary inflammation ultimately causing neurologic dysfunction/cell death. Animal model and early human studies of ALS suggest that regulation of inflammation at the macrophage level may mitigate this process resulting in slowing or reversing the inflammation associated neurodegenerative process.

Chlorite composition has also been tested in Phase 1 and 2 clinical trials in ALS patients and shown to decrease markers of inflammation after a single dose. In Phase 1, following chlorite treatment, changes in monocyte levels of HLA-DR did not demonstrate a dose-dependent effect; however, HLA-DR expression was down-regulated at all doses of chlorite composition in patients with the high baseline levels of monocyte HLA-DR The placebo group showed relatively stable monocyte HLA-DR after treatment. The changes of HLA-DR expression on monocytes in the chlorite treatment response were linearly related to the degree of baseline monocyte HLA-DR expression 24 h after treatment. The greater the starting monocyte HLA-DR levels at baseline the greater the HLA-DR response to chlorite treatment. In the group of patients with elevated baseline monocyte HLA-DR, the average percent change from baseline 24 h after chlorite treatment was more than 10%, whereas those patients with lower range monocyte HLA-DR showed no change from baseline.

Dose-dependent changes in chlorite treated patients compared to placebo were observed in the level of CD16 expression on the CD16 bright subset of monocytes. There was no significant change in the level of monocyte CD16 expression in the placebo group. Twenty-four hours after one dose of chlorite treatment, the difference between the ALS and normal control level of monocyte CD16 expression was reduced by approximately 50% toward the normal value compared with baseline pretreatment levels in the ALS patients.

In the Phase 2 clinical trials in ALS patients, slowing of progression was observed in the high-dose group, in patients with greater inflammation (e.g., higher levels of C-reactive protein (CRP)). Moreover, chlorite composition may have dose-dependently halted symptom progression in a subset of patients. More than 2 times as many patients on high dose chlorite composition (25%) did not progress during six months of treatment compared to placebo (11%). Most "responders" had an elevated biomarker of inflammation, IL-18, and were positive for LPS at baseline which decreased following treatment with chlorite composition. No toxicities were noted in either the phase 1 or 2 trials. These clinical data provided compelling rationale to test chloride composition in pre-clinical models of Parkinson's disease to investigate its brain penetrance, ability to modulate microglia activation and peripheral immune cell infiltration to the CNS, and protect vulnerable neuronal populations from synuclein-induced degeneration.

Taken together, these clinical data provided strong compelling rationale to test chlorite composition in pre-clinical models of Parkinson's Disease. Chlorite composition modulates immune cells away from a pro-inflammatory (M1-like) activated phenotype and towards a wound-healing/protective (M2-like) phenotype and ameliorates neuroinflammation and infiltration of peripheral immune cells into the CNS. In doing so, it attenuates, slows down, or halts the course of degeneration in patients with underlying neuroinflammation. In addition, this study demonstrates whether direct immunomodulation of microglia/monocyte phenotypes can affect synuclein deposition/clearance.

Depression

In various embodiments, the disease is depression. In various embodiments the disease is major depressive disorder, treatment resistant major depressive disorder, recurrent depressive disorder, dysthymia, bipolar I depression, bipolar II depression, mixed depression and anxiety, a depressive psychotic episode, atypical depression, seasonal depressive disorder, brief recurrent depressive disorder, postpartum depression, or depression with catatonic features.

In various embodiments, the disease is depression. Symptoms of depression include, but are not limited to, depressed mood, irritability, decreased interest or pleasure, significant weight change, change in appetite, change in sleep, hypersomnia, insomnia, psychomotor agitation or retardation, fatigue or loss of energy, feelings of worthlessness or excessive or inappropriate guilt, diminished ability to think or concentrate, or more indecisiveness, thoughts of death or suicide. In various embodiments, the chlorite compound is used to reduce or treat symptoms of depression.

Immune abnormalities are important features of pathophysiology and the treatment of psychiatric disorders including major depression. In various embodiments, the patient with depression has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-$\alpha$, soluble TNF receptor-1, and/or IL-1 receptor antagonist. In various embodiments, cytokine levels are reduced in a patient with depression by administration of a chlorite compound. In various embodiments the individual with depression has increased C-reactive protein (CRP), a commonly available marker of systemic inflammation. In various embodiments, treatment with the chlorite compound reduces levels of C-reactive protein. In various embodiments, the chlorite compound reduces or corrects these immune abnormalities thereby reducing or treating the symptoms of depression. In various embodiments, pretreatment levels of CRP predicts responsiveness to efficacy of treatment with a chlorite composition. In various embodiments, levels of CRP are used to determine type of antidepressant treatment to use, and whether a chlorite composition is appropriate for treatment of depression in an individual.

Bipolar Disorder

In various embodiments, the disease is bipolar disorder. In various embodiments the disease is bipolar I depression, bipolar II depression, or cyclothymic bipolar disorder. In various embodiments, the bipolar disorder is rapid cycling or treatment resistant bipolar disorder.

In various embodiments, the disease is bipolar disorder. Symptoms of bipolar disorder include, but are not limited to, major depressive episodes, hypomanic episodes, manic episodes, psychosis, unpredictable changes in mood and behavior, inflated self-esteem or grandiosity, decreased need for sleep, unusual talkativeness, racing thoughts, increased distractibility. In various embodiments, the chlorite compound is used to treat or reduce symptoms of bipolar disorder.

Immune abnormalities are important features of pathophysiology and the treatment of psychiatric disorders including bipolar disorder. In various embodiments, the patient with bipolar disorder has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-$\alpha$, soluble TNF receptor-1, and/or IL-1 receptor antagonist. In various embodiments, cytokine levels are reduced in a patient with bipolar disorder by administration of a chlorite compound. In various embodiments, the chlorite compound reduces or corrects these immune abnormalities thereby reducing or treating the symptoms of bipolar disorder.

Posttraumatic Stress Disorder

In various embodiments, the disease is posttraumatic stress disorder. In various embodiments, the disease is posttraumatic stress disorder—dissociative subtype.

In various embodiments, the disease is posttraumatic stress disorder. Symptoms of posttraumatic stress disorder include, but are not limited to, intrusive memories; recurrent, unwanted distressing memories of the traumatic event; reliving a traumatic event as if it were happening again (flashbacks); upsetting dreams about the traumatic event; severe emotional distress or physical reactions to something that reminds you of a traumatic event; avoidance behavior; trying to avoid thinking or talking about a traumatic event; avoiding places, activities or people that remind one of a traumatic event; negative changes in thinking and mood; negative self-esteem; inability to experience positive emotions; emotional numbness; feelings of hopelessness; memory problems; difficulty maintaining close relationships; changes in emotional reactions; irritability, angry outbursts or aggressive behavior; self-destructive behavior; trouble concentrating; trouble sleeping; being easily startled or frightened. In various embodiments, the chlorite compound reduces or treats symptoms of posttraumatic stress disorder.

Immune abnormalities are important features of pathophysiology and the treatment of psychiatric disorders including posttraumatic stress disorder. In various embodiments the patient with posttraumatic stress disorder has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with posttraumatic stress disorder by administration of a chlorite compound. In various embodiments, the chlorite compound reduces or corrects these immune abnormalities thereby reducing or treating the symptoms of posttraumatic stress disorder.

Schizophrenia

In various embodiments, the disease is schizophrenia. In various embodiments, the schizophrenia is characterized as one of five subtypes: paranoid, disorganized, catatonic, undifferentiated, or residual.

In various embodiments, the disease is schizophrenia. Symptoms of schizophrenia include, but are not limited to, delusions; hallucinations; disorganized thinking (speech); disorganized or abnormal motor behavior. In various embodiments, the chlorite compound reduces or treats symptoms of schizophrenia.

Immune abnormalities are important features of pathophysiology and the treatment of psychiatric disorders including schizophrenia. In various embodiments, the patient with schizophrenia has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with schizophrenia by administration of a chlorite compound. In various embodiments, the chlorite compound reduces or corrects these immune abnormalities thereby reducing or treating the symptoms of schizophrenia.

Autism

In various embodiments, the disease is autism. In various embodiments, the disease is autism spectrum disorder.

In various embodiments, the disease is autism or autism spectrum disorder. Symptoms of autism or autism spectrum disorder include, but are not limited to, deficits in social interactions and relationships; significant problems developing nonverbal communication skills, such as eye-to-eye gazing, facial expressions and body posture; failure to establish friendships with children the same age; lack of interest in sharing enjoyment, interests, or achievements with other people; lack of empathy; delay in or lack of learning to talk; stereotyped and repetitive use of language, limited interest in activities or play; unusual focus on particular options; preoccupation with certain topics; need for sameness and routines and stereotyped behaviors. In various embodiments, the chlorite compound reduces or treats symptoms of autism or autism spectrum disorder.

Immune abnormalities are important features of pathophysiology and the treatment of psychiatric disorders including autism. In various embodiments, the patient with autism demonstrates oxidative stress, mitochondrial dysfunction and/or immune dysregulation/inflammation in the brain. In various embodiments, the patient with autism shows elevated levels of corticotrophin-releasing hormone, neurotensin or mTOR activity. In various embodiments, the brain of the individual with autism shows increased microglial activation. In various embodiments the patient with autism has elevation of proinflammatory, anti-inflammatory, and/or regulatory cytokines. In various embodiments, an individual has elevated IL-4, IL-6, IL-10, soluble IL-2 receptor, soluble IL-6 receptor, tumor necrosis factor (TNF)-α, soluble TNF receptor-1, and/or IL-1 receptor antagonist. In various embodiments, cytokine levels are reduced in a patient with autism by administration of a chlorite compound. In various embodiments, the chlorite compound reduces or corrects these immune abnormalities thereby reducing or treating the symptoms of autism.

Duchenne's Muscular Dystrophy (DMD)

In various embodiments, the disease is Duchenne's muscular dystrophy (DMD). Genetic diseases that are triggered by LPS, such as ALS and FTD, may have shared monocytic/macrophage activation pathways with additional diseases that would be targets for chlorite-mediated regulation. One example of such a disease is DMD. In some embodiments, DMD is driven by the activation of the LPS receptor on the macrophage. Animal studies have proven that knocking out of the LPS receptor, toll like receptor 4 (TLR4), severely reduces the disease progression observed. As such, DMD may respond to a chlorite composition.

Chlorite Compositions & Modes of Administration

In various embodiments, chlorite composition is a composition that is greater than 99% pure form of sodium chlorite (stabilized with phosphate buffer to a pH of 8) for use intravenously as an immunomodulatory drug to convert M1 antigen presenting cells, including peripheral monocytes, to an M2 protective phenotype. When administered in vivo chlorite is converted to hypochlorite at the surface of macrophages through interactions with heme-associated iron and the hypochlorite is converted to a long-lived intracellular chloramine after interaction with intracellular taurine. Chlorite's metabolic byproducts are water and oxygen. Intracellular chloramines regulate inflammatory pathways such as NF-kB and caspase-mediated pathways to reprogram inflammatory macrophages to their innate phagocytic wound-healing forms. Reversal of the monocyte and macrophage inflammatory phenotype results in down regulation of cell surface activation markers such as CD16 and HLA-DR. Chlorite is not immunosuppressive as it enhances the innate immune system while regulating inflammation.

Methods of administering chlorite to a subject are provided. In various embodiments, the method comprises intravenously administering a therapeutically effective amount of an aqueous pharmaceutical formulation comprising chlorite, and a saline solution. In one embodiment, the chlorite composition contains purified sodium chlorite with no greater than about 0.6% of sulfate ions or 1.4% of chlorate ions.

In various embodiments, the pH of the aqueous pharmaceutical formulation comprising chlorite is about 7 to about 11, preferably about 7 to about 9.5. In various embodiments, the pH is between 7.5 and 9. In various embodiments, the aqueous pharmaceutical formulation includes a buffer. Buffers include phosphate buffers, borate buffers, citrate buffers, carbonate buffers, and the like. In one embodiment, the buffer is a phosphate buffer such as monosodium phosphate or disodium phosphate. In some embodiments, any of the formulations or pharmaceutical formulations described herein comprises a pH adjusting agent that consists essentially of phosphate.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are Water for Injection (WFI, USP), Sterile Water for Injection (SWFI, USP), Ringer's solution, USP, and isotonic solution, such as isotonic sodium chloride solution. In addition, sterile, fixed oils are conventionally employed as a solvent or suspending medium. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In various embodiments, the injectable formulations are sterile, pyrogen free, and free of particulates according to USP-NF standards. Preferably, the sterility, pyrogenicity, and particulates assays are conducted according to USP-NF protocols.

In various embodiments, the pharmaceutically acceptable chlorite salt is administered in an amount ranging from 0.1 to 10 mg/kg body weight, such as about 1 mg/kg body weight. The pharmaceutically acceptable salt may be administered by intravenous infusion, such as over a period ranging from about 0.5 to about 4 hours. In various embodiments, the chlorite salt is administered more than once in a month, such as at least once per week for a period of at least one month. In various embodiments, the chlorite salt is administered for at least a year.

Methods of formulating chlorite have been described in US Patent Pub. No. 20070145328, filed Dec. 21, 2006 and entitled "Chlorite Formulations, and Methods of Preparation and Use Thereof," which is incorporated herein by reference in its entirety. Such formulations are suitable for various modes of administration, including but not limited to non-topical, parenteral, systemic, or intravenous administration.

In some embodiments, the present invention makes use of chlorite formulated in aqueous solution in which the chlorite is 97-99% pure. As used herein, the "purity" of chlorite in a sample is calculated as the percent weight of chlorite salt to the total weight of the sample. In determining the purity of chlorite in a solution, the weight of the solvent (e.g., water as an aqueous solution) is not included. Purity may be evaluated using ion chromatography and an ion detector, by calibrated integration of the respective peaks; for example, chlorite, chloride, chlorate, phosphate and sulfate in the compound or formulation. For example, chlorite is commercially available as sodium chlorite, technical grade, at a purity of 80% (catalog No. 244155 Sigma-Aldrich).

Alternatively, crystalline sodium chlorite is provided in a purity greater than 95%, greater than 96%, greater than 97%, greater than 98%, greater than 99%, or greater than 99.9%. Solid pharmaceutical formulations comprising crystalline sodium chlorite in a purity greater than 95%, greater than 96%, greater than 97%, greater than 98%, greater than 99%, or greater than 99.9% in addition to one or more pharmaceutical excipients are also encompassed.

In some embodiments, the chlorite formulations for use with the present invention comprise low amounts of chlorate, sulfate or chloride. As used herein, a formulation is "substantially free" of a molecule if the molecule comprises no more than 1 part in 1000 per weight of non-solvent molecules in the formulation. In certain embodiments, the weight ratio of chlorite to chlorate is greater than 100:1.5, greater than 100:1, greater than 100:0.5, or greater than 100:0.1. In one embodiment, the composition is substantially free of chlorate. In another embodiment, the weight ratio of chlorite to chloride is greater than 100:45.5 or greater than 100:8.5. In one embodiment the composition is substantially free of chloride. In a further embodiment, the weight ratio of chlorite to sulfate is greater than 100:16.4 or greater than 100:1.6. In one embodiment the composition is substantially free of sulfate.

The pH of a chlorite formulation for use with the present invention can be adjusted to between about 7 and about 11.5. In some embodiments, the pH of a chlorite formulation is lowered to between about 7 and about 11.5 using a pH adjusting compound that does not expose the formulation to high local acidity. In some embodiments, the pH adjusting compound is any one or more of monosodium phosphate, disodium phosphate, or acetic acid.

The formulations may have differing concentration of chlorite. In some embodiments, the concentration of chlorite in the formulation is high, and then is diluted to a less concentrated form prior to administration. In some embodiments, a formulation described herein is diluted any of about 2.5×, about 5×, about 7.5×, about 10×, about 20×, about 25×, about 50×, about 100×, about 200×, about 250×, about 300×, about 500×, or about 1000×. In some embodiments, a formulation described herein is diluted about 2.5×, about 5×, about 10×, about 20×, about 25×, about 50×, about 100×, about 200×, about 250×, about 300×, about 500×, about 1000×; between about 2× and about 10×, between about 10× and about 50×, between about 50× and about 100×, between about 100× and about 500×, or between about 500× and about 1000×. In some embodiments, a formulation as described herein is diluted between about 2× and about 10×. In some embodiments, a formulation as described herein is diluted between about 10× and about 50×. In some embodiments, a formulation as described herein is diluted about 7.5×. In some embodiments, a formulation as described herein is diluted about 25×. In some embodiments, a formulation as described herein is diluted about 200×. In some embodiments, the concentration of chlorite in the formulations described herein is between about 1 µM and about 1.5 M. In another embodiment, the concentration of chlorite in the formulations described herein is between any of about 1 M and about 1.5 M; between about 1 µM and about 100 mM; between about 10 µM and about 100 mM; between about 0.1 mM and about 10 mM; between about 0.1 mM and about 500 mM; between about 0.1 mM and about 200 mM; between about 1 mM and about 100 mM; between about 0.1 mM and about 5 mM; between about 50 mM and about 100 mM; between about 55 mM and about 70 mM; between about 60 mM and about 65 mM; between about 100 mM and about 500 mM; between about 200 mM and about 400 mM; between about 300 mM and about 700 mM; about 1 mM; about 1.5 mM; about 2 mM; about 2.5 mM; about 3 mM; about 3.5 mM; about 4 mM; about 5 mM; about 10 mM; about 20 mM; about 30 mM; about 40 mM; about 50 mM; about 60 mM; about 62 mM; about 65 mM; about 70 mM; about 80 mM; about 90 mM; about 100 mM; at least about 0.1 mM; at least about 1 mM; at least about 2 mM; at least about 5 mM; at least about 10 mM; at least about 20 mM; at least about 30 mM; at least about 40 mM; at least about 50 mM; at least about 60 mM; at least about 70 mM; at least about 80 mM; at least about 90 mM; or at least about 100 mM. In some embodiments, the concentration of chlorate in the formulations described herein is between about 50 mM and about 100 mM. In some embodiments, the concentration of chlorate in the formulations described herein is between about 55 mM and about 75 mM. In some embodiments, the concentration of chlorate in the formulations described herein is between about 0.1 mM and about 10 mM. In some embodiments, the concentration of chlorate in the formulations described herein is between about 1 mM and about 5 mM.

In some embodiments, the chlorite formulations described herein contain less than about 1.9% of chloride ions. In some embodiments, the chlorite formulation contains any of less than about 1.9%, less than about 1.8%; less than about 1.5%; less than about 1.0%; less than about 0.5%; less than about 0.3%; less than about 0.1%; less than about 0.05%; less than about 0.01%; less than about 0.001%; between about 0.001 to about 0.1%; between about 0.1 to about 0.5%; between about 0.5 to about 1.0%; between about 1.0 to about 1.5%; or between about 1.5 to about 1.8% by weight of chloride ions.

In some embodiments, the chlorite formulation contains less than about 1.5% of chlorate ions. In some embodiments, the chlorite formulation contains any of less than about 1.4%, less than about 1.3%; less than about 1.0%; less than about 0.5%; less than about 0.3%; less than about 0.1%; less than about 0.01%; less than about 0.001%; between about 0.001 to about 0.1%; between about 0.001 to about 0.01%; between about 0.01 to about 0.1%; between about 0.1 to about 0.5%; between about 0.5 to about 1.0%; or between about 1.0 to about 1.4% of chlorate ions. In some embodiments, the chlorite formulation is substantially free of chlorate ions. In some embodiments, the chlorite formulation contains less than about 0.5% by weight of chlorate ions. In some variations, the chlorite formulation is substantially free of chlorate ions. In some embodiments, the chlorite formulation contains less than about 0.19% by weight of chlorate ions. In some embodiments, the chlorite formulation contains less than about 0.1% by weight of chlorate ions. In some embodiments, the level of chlorate ions is below the level of detection using HPLC.

In some embodiments, the chlorite formulation contains less than about 0.7% of sulfate ions. In some embodiments, the chlorite formulation contains any of less than about 0.65%; less than about 0.6%; less than about 0.5%; less than about 0.4%; less than about 0.3%; less than about 0.2%; less than about 0.1%; less than about 0.08%; less than about 0.07%; less than about 0.06%; less than about 0.05%; less than about 0.005%; less than about 0.0005%; between about 0.001 to about 0.1%; between about 0.01 to about 0.1%; between about 0.01 to about 0.5%; between about 0.06 to about 0.08%; or between about 0.5 to about 0.65% of sulfate ions. In some embodiments, the chlorite formulation contains between about 0.5 to about 0.65% of sulfate ions. In some embodiments, the chlorite formulation is substantially free of sulfate ions. In some embodiments, the chlorite formulation contains less than about 0.5% by weight of sulfate ions. In some embodiments, the chlorite formulation is substantially free of sulfate ions. In some embodiments, the chlorite formulation contains less than about 0.08% by weight of sulfate ions. In some embodiments, the level of sulfate ions is below the level of detection using HPLC.

In some embodiments, the chlorite formulation contains less than about 0.5% by weight of chloride ions. In some embodiments, the chlorite formulation contains less than about 0.24% by weight of chloride ions. In some embodiments, the chlorite formulation contains less than about 0.2% by weight of chloride ions. In some embodiments, the chlorite formulation contains less than about 0.1% by weight of chloride ions. In some embodiments, the chlorite formulation is substantially free of chloride ions. In some embodiments, the level of chloride ions is below the level of detection using HPLC.

In some embodiments, the chlorite formulations described herein comprise phosphate ions. In some embodiments, the chlorite formulations described herein comprise sodium ions. In some embodiments, a chlorite formulation comprises chlorite, an aqueous solvent, sodium, and phosphate ions. In some variations, the aqueous solvent consists essentially of water. In some embodiments, a chlorite formulation consists essentially of chlorite, water, sodium, and phosphate, and is substantially free of chlorate. In some embodiments, a chlorite formulation consists essentially of chlorite, water, sodium, and phosphate, and is substantially free of chlorate, and further comprises a pharmaceutically acceptable diluent. In some embodiments, sodium and phosphate are provided in whole or in part as monosodium phosphate or disodium phosphate. In some embodiments, the pharmaceutically acceptable diluent is a saline solution.

In some embodiments, the chlorite formulations described herein comprise no greater than about 10% by weight of by products or impurities present in commercially available technical grade chlorite. Non-limiting examples of by-products or impurities present in commercially available technical grade chlorite include chlorate, sulfate, chlorine dioxide, chloride, sodium bicarbonate, and sodium carbonate. In some embodiments, the chlorite formulations described herein comprise no greater than about any of 15%, about 12%, about 10%, about 9%, about 8%, about 7%, about 6%, about 5%, about 4%, about 3%, about 2%, about 1%, about 0.5%, about 0.3%, about 0.1%, between about 0.1 to about 5%; between about 5 to about 10%; or between about 10 to about 15% by weight of one or more degradation products or impurities present in commercially available technical grade chlorite, including but not limited to one or more of chlorate or sulfate. In some embodiments, the chlorite formulations described herein comprise no greater than about 0.5% by weight of degradation products or impurities present in commercially available technical grade chlorite, including but not limited to one or more of chlorate or sulfate. In some embodiments, the chlorite formulations described herein comprise no greater than about 5% by weight of degradation products or impurities present in commercially available technical grade chlorite, including but not limited to one or more of chlorate or sulfate. In some embodiments, the chlorite formulations described herein are substantially free of the degradation products or impurities present in commercially available technical grade chlorite, including but not limited to chlorate or sulfate.

Chlorite formulations are generally dosed in vivo corresponding to the body weight of the subject. Due to the continuous breakdown of the active agent in the blood, the agent is normally administered at regular intervals. Those of skill in the art will readily appreciate that actual dosages and regimen will vary as a function of the agent, formulation, the severity of the symptoms, the susceptibility of the subject to treatment and/or side effects, and the like. Dosages are readily and routinely determined by those of skill in the art by a variety of means.

In some embodiments, the formulations described herein are less toxic to a subject than previously reported chlorite formulations at the same concentration of chlorite, when administered by at least one of the routes of administration described herein, including but not limited to by non-topical, systemic, parenteral, or intravenous administration. In some embodiments, the toxicity of a chlorite formulation is analyzed for toxicity using an in vivo or in vitro toxicity assay, including well-known toxicity assays. In some embodiments, the chlorite formulation is analyzed for toxicity using a nonspecific in vitro toxicity assay.

The regimen of administration—e.g., dose combined with frequency of administration—will generally involve administration in an amount and at a frequency to provide a desired effect. For example, chlorite or a chlorite-containing agent can be administered for 2, 3, 4, 5, 6, 7, 8, 9, 10 or more consecutive days, which administration period may be reinitiated after 1, 2, 3 or more weeks following the last dose.

Chlorite according to the invention may be administered on a daily basis. Chlorite according to the invention may be administered once. Chlorite may be administered weekly. Chlorite may be administered from about once a week to about once a day. In some embodiments, chlorite is administered at a dose of about 0.2 mg/kg/day of chlorite to about 3.3 mg/kg/day of chlorite. In some embodiments, chlorite is administered at a dose of about 0.2 mg/kg/day of chlorite, about 0.4 mg/kg/day of chlorite, about 0.5 mg/kg/day of chlorite, about 0.6 mg/kg/day of chlorite, about 0.7 mg/kg/day of chlorite, about 0.8 mg/kg/day of chlorite, about 0.9 mg/kg/day of chlorite, about 1.0 mg/kg/day of chlorite, about 1.1 mg/kg/day of chlorite, about 1.2 mg/kg/day of chlorite, about 1.3 mg/kg/day of chlorite, about 1.4 mg/kg/day of chlorite, about 1.5 mg/kg/day of chlorite, about 1.6 mg/kg/day of chlorite, about 1.7 mg/kg/day of chlorite, about 1.8 mg/kg/day of chlorite, about 1.9 mg/kg/day of chlorite, about 2.0 mg/kg/day of chlorite, about 2.1 mg/kg/day of chlorite, about 2.2 mg/kg/day of chlorite, about 2.3 mg/kg/day of chlorite, about 2.4 mg/kg/day of chlorite, about 2.5 mg/kg/day of chlorite, about 2.6 mg/kg/day of chlorite, about 2.7 mg/kg/day of chlorite, about 2.8 mg/kg/day of chlorite, about 2.9 mg/kg/day of chlorite, about 3.0 mg/kg/day of chlorite, about 3.1 mg/kg/day of chlorite, about 3.2 mg/kg/day of chlorite, about 3.3 mg/kg/day of chlorite, about 3.4 mg/kg/day of chlorite, or about 3.5 mg/kg/day of chlorite. Chlorite may be administered at a dose of about 1 mg/kg/day. Chlorite may be administered at a dose of about 2 mg/kg/day. Chlorite may be administered at a dose of 1 mg/kg/day. Chlorite may be administered at a dose of 2 mg/kg/day.

In some embodiments, chlorite is administered on a daily basis at a dose of about 0.2 mg/kg/day of chlorite to about 3.3 mg/kg/day of chlorite. In some embodiments, chlorite is administered on a daily basis at a dose of about 0.2 mg/kg/day of chlorite, about 0.4 mg/kg/day of chlorite, about 0.5 mg/kg/day of chlorite, about 0.6 mg/kg/day of chlorite, about 0.7 mg/kg/day of chlorite, about 0.8 mg/kg/day of chlorite, about 0.9 mg/kg/day of chlorite, about 1.0 mg/kg/day of chlorite, about 1.1 mg/kg/day of chlorite, about 1.2 mg/kg/day of chlorite, about 1.3 mg/kg/day of chlorite, about 1.4 mg/kg/day of chlorite, about 1.5 mg/kg/day of chlorite, about 1.6 mg/kg/day of chlorite, about 1.7 mg/kg/day of chlorite, about 1.8 mg/kg/day of chlorite, about 1.9 mg/kg/day of chlorite, about 2.0 mg/kg/day of chlorite, about 2.1 mg/kg/day of chlorite, about 2.2 mg/kg/day of chlorite, about 2.3 mg/kg/day of chlorite, about 2.4 mg/kg/day of chlorite, about 2.5 mg/kg/day of chlorite, about 2.6 mg/kg/day of chlorite, about 2.7 mg/kg/day of chlorite, about 2.8 mg/kg/day of chlorite, about 2.9 mg/kg/day of chlorite, about 3.0 mg/kg/day of chlorite, about 3.1 mg/kg/day of chlorite, about 3.2 mg/kg/day of chlorite, about 3.3 mg/kg/day of chlorite, about 3.4 mg/kg/day of chlorite, or about 3.5 mg/kg/day of chlorite.

In some embodiments, the chlorite is administered at a dose and frequency that results in a reduction of an inflammatory marker in a sample of the subject. The inflammatory marker may be any inflammatory marker disclosed herein or combinations thereof. The sample may be selected from a blood sample, urine sample, plasma sample, cerebrospinal fluid, or any other biological sample described herein. The reduction may be at least 10%. The reduction may be at least 15%. The reduction may be at least 20%. The reduction may be at least 25%. The reduction may be at least 30%. The reduction may be about 5% to about 100%. The reduction may be about 5% to about 75%. The reduction may be about 5% to about 50%. The reduction may be maintained for at least a week, at least a month, at least six months, or at least one year, or indefinitely. The reduction may be maintained as long as the subject continues to be administered the chlorite. The reduction may be achieved with a first dose at a first frequency, and maintained at a second dose at a second frequency. The first dose and the second dose may be the same. The first dose and the second dose may be different. The dose may be a dose disclosed herein. The first frequency and the second frequency may be the same. The first frequency and the second frequency may be different. The frequency may be a frequency disclosed herein.

In some embodiments, the pharmaceutical composition used in the methods of the invention can be further administered in a cycle. An exemplary cycle consists of: a) a first period of time wherein the pharmaceutical composition is administered at a first dose for a first number of times; and b) a second period of time wherein the pharmaceutical composition is administered at a second dose for a second number of times. In some embodiments, the first period of time is about one week, the first number of times is about five, the second period of time is about two weeks, and the second number of times is zero. In other embodiments, the first period of time is about one week, the first number of times is about three, the second period of time is about one week, and the second number of times is zero. The first dose can be about 0.4 mg/kg/day of chlorite to about 3.3 mg/kg/day of chlorite. For example, the first dose can be about 2.1 mg/kg/day of chlorite. The cycle can be performed multiple times, e.g., about 2, 3, 4, 5, 6, 7, 8, 9, 10 or 10 or more times. In some embodiments, the cycle is performed about 2-4 times.

In some embodiments, the dosing schedule consists of periods of administration alternating with periods of non-administration. For example, chlorite might be administered in a three week cycle, comprising dosing chlorite up to 5 times in a week followed by two weeks without treatment.

The cycle could be repeated as necessary to achieve the desired result. In another embodiment, chlorite is administered in a two week cycle, e.g., up to 3 times in a week followed by a week without administration. In some embodiments, a total of 2-4 cycles are performed. In an exemplary embodiment, the dosing regimen comprises administration of 2.1 mg/kg/day of chlorite for a total of 2-4 three week cycles.

In certain embodiments, the administration of pharmaceutical compositions of the present invention further comprises one or more additional therapeutically active ingredients (e.g., anti-inflammatory and/or palliative).

All of the compositions and pharmaceutical formulations described herein may be used in kits. In some embodiments, the kits are intended for administration of chlorite or a chlorite-containing agent, or pharmaceutical formulations comprising such agents. The kits may include a unit dosage amount of the agents or formulations as described herein. In some variations, the kits comprise suitable packaging. In some variations, the kits comprise instructions for use of the active agent in a neurodegenerative disease as described above. In a non-limiting example, the kit may contain instructions for using chlorite formulations to treat macrophage related symptoms of a neurodegenerative disease as described above. Accordingly, the kits may be used for any of the treatment methods described herein, and in some embodiments contain suitable instructions for practicing any of the treatment methods described herein. In some embodiments, the kits are used to treat any one or more of the diseases or conditions described herein. Kits may also comprise an aid to administration of the active agent formulation, such as an inhaler, spray dispenser (e.g., nasal spray), syringe for injection or pressure pack for capsules, tablets, or suppositories.

EXAMPLES

Example 1: Treatment of ALS Patients with sodium chlorite

Both phase 1 and 2A clinical trials using sodium chlorite in patients with ALS were completed. Sodium chlorite reversed markers of monocyte/macrophage activation in vitro and in vivo. In a double blind phase 2 study of sodium chlorite response to therapy was evaluated using a robust measurement of ALS disease activity termed the ALS functional rating scale-revised (ALS/FRS-R). The ALS-FRS is described by Cederbaum et al. (Journal of Neurological Sciences, vol 169, pp. 13-21). 25% of patients receiving the high dose of sodium chlorite (2 mg/kg) stopped progressing over a six month period as compared to placebo patients who had only a 10% non-progressor rate. This difference was statistically significant. Biomarkers that were associated with the group of patients whose disease halted during the trial (responders) showed several inflammatory biomarkers to be twice as high at baseline as compared to those patients who did not respond to sodium chlorite (progressors). These plasma markers included: IL18, gamma interferon, IL6 and CRP. Also noted was that plasma wide range CRP (wr-CRP) levels (a general plasma biomarker associated with systemic inflammation) obtained at baseline allowed division of patients into those above the median level for all patients in trial (1125 ng/ml as median value). There was a dose dependent slowing of disease progression in patients with above the median wr-CRP value such that patients receiving 2 mg/kg progressed at a 44% slower rate than the placebo patients over the six months of study.

Figure 2:
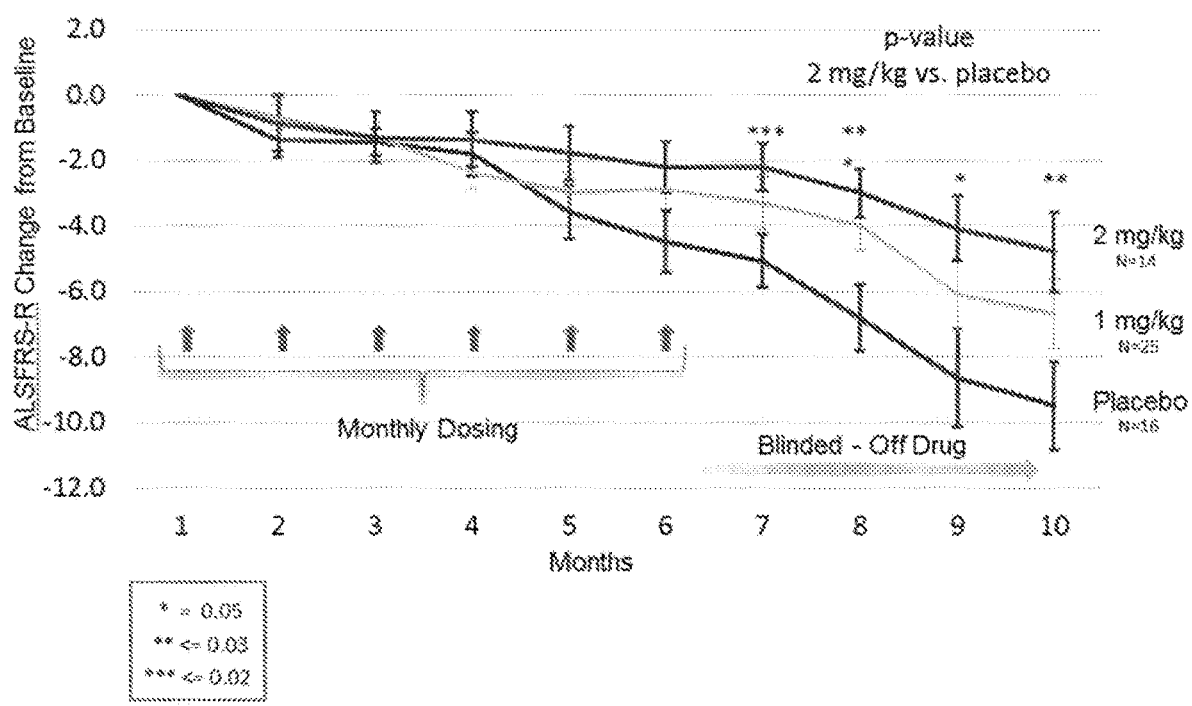
FIG. 2 demonstrates sodium chlorite delay of disease progression in ALS patients with greater systemic inflammation.
Figure 3:
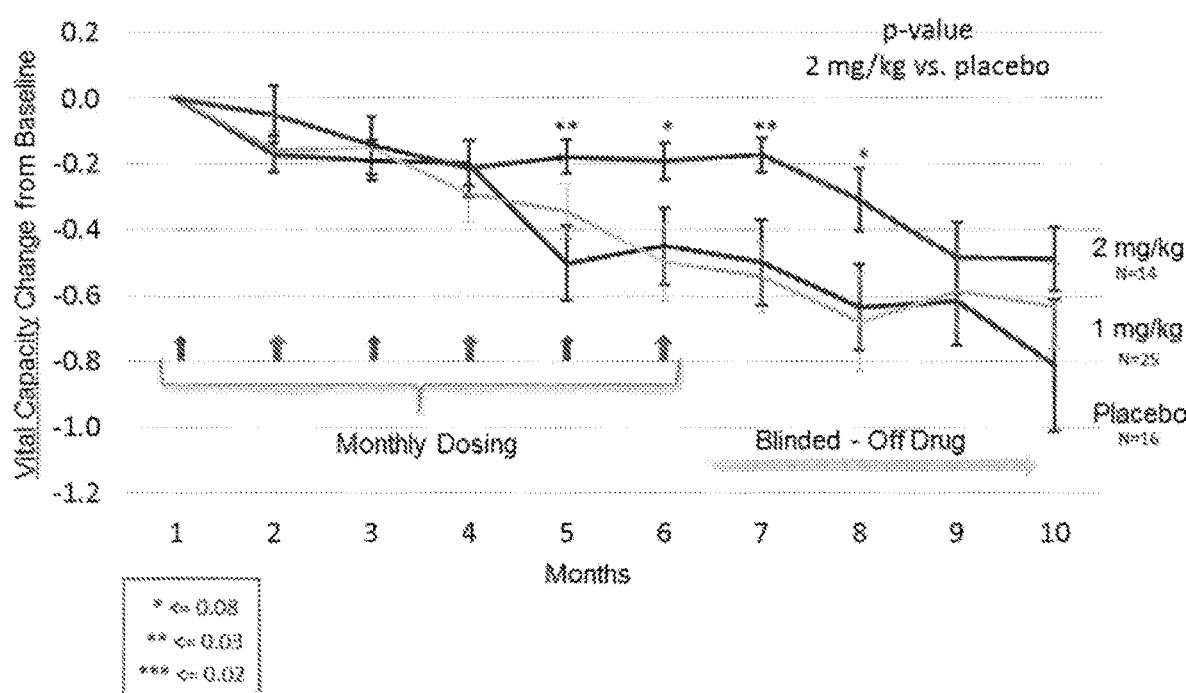
FIG. 3 demonstrates sodium chlorite maintains vital capacity in ALS patients with greater systemic inflammation as measured by lung vital capacity as a change from baseline.

An analysis of the data using a change from baseline in ALS/FRS-R values during the 6 months of treatment and an additional 3 month follow-up showed a highly significant slowing of ALS disease progression in a dose dependent manner (see FIG. 2). Additionally, change from baseline in forced vital capacity, a quantitative measure of breathing efficiency showed a significantly slower rate of progressive loss in breathing function in the 2 mg/kg group as compared to controls (see FIG. 3). These data were consistent with having identified a group of ALS patients using baseline biomarker levels such as wr-CRP, who when treated with sodium chlorite, a macrophage activation regulator, slow or halt disease progression during a treatment period.

Example 2: Treatment of FTD Patients with Sodium Chlorite

Figure 4A:
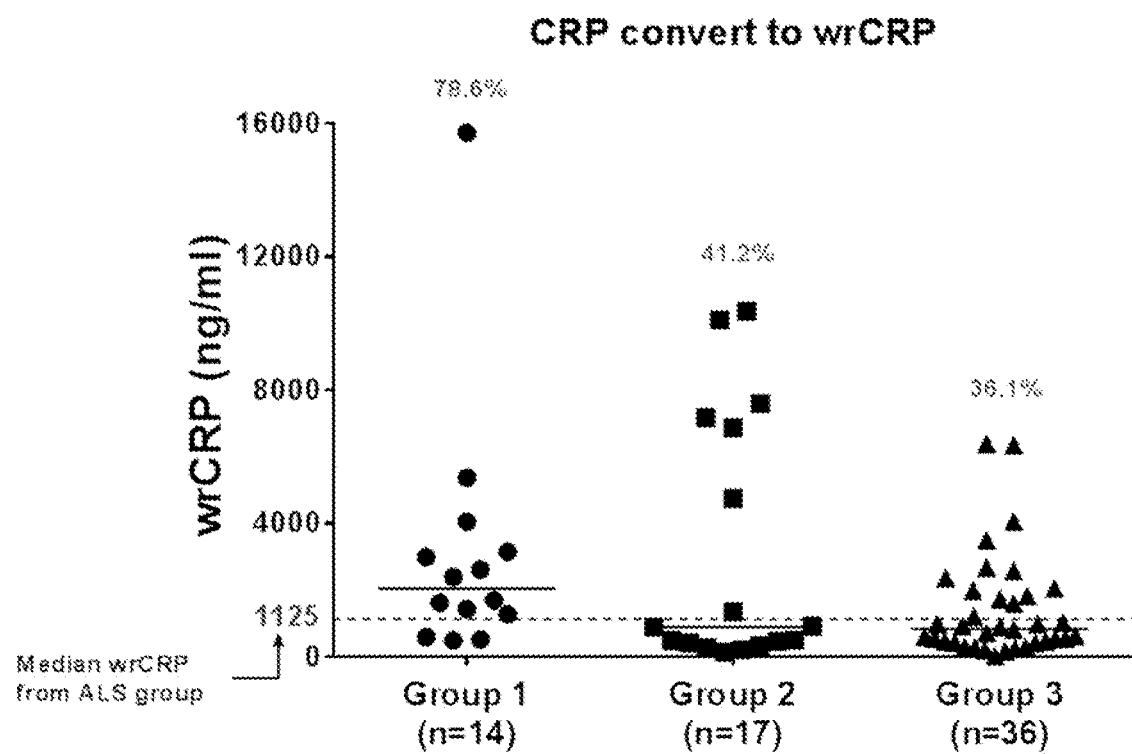
FIG. 4A shows a group of FTD patients having wr-CRP levels higher than controls and patients with ALS.
Figure 4B:
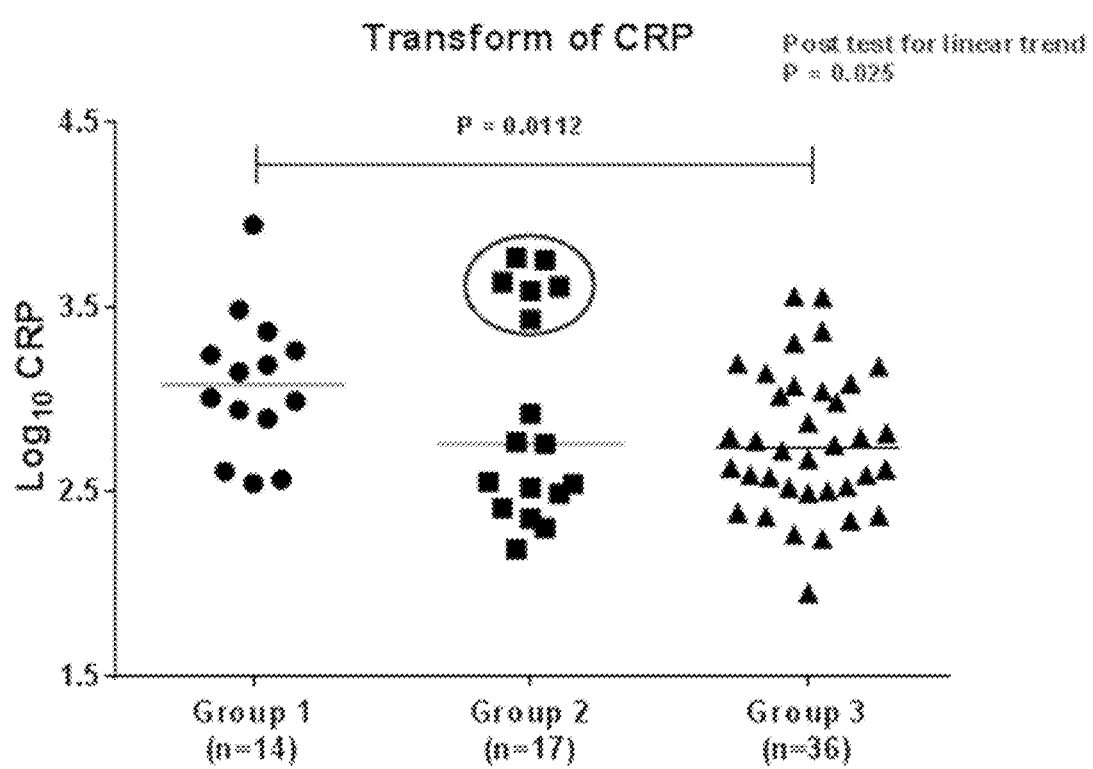
FIG. 4B shows FTD patients have elevation of plasma hs-CRP. ⅓ of PGN+/− carriers are also elevated.
Figure 4C:
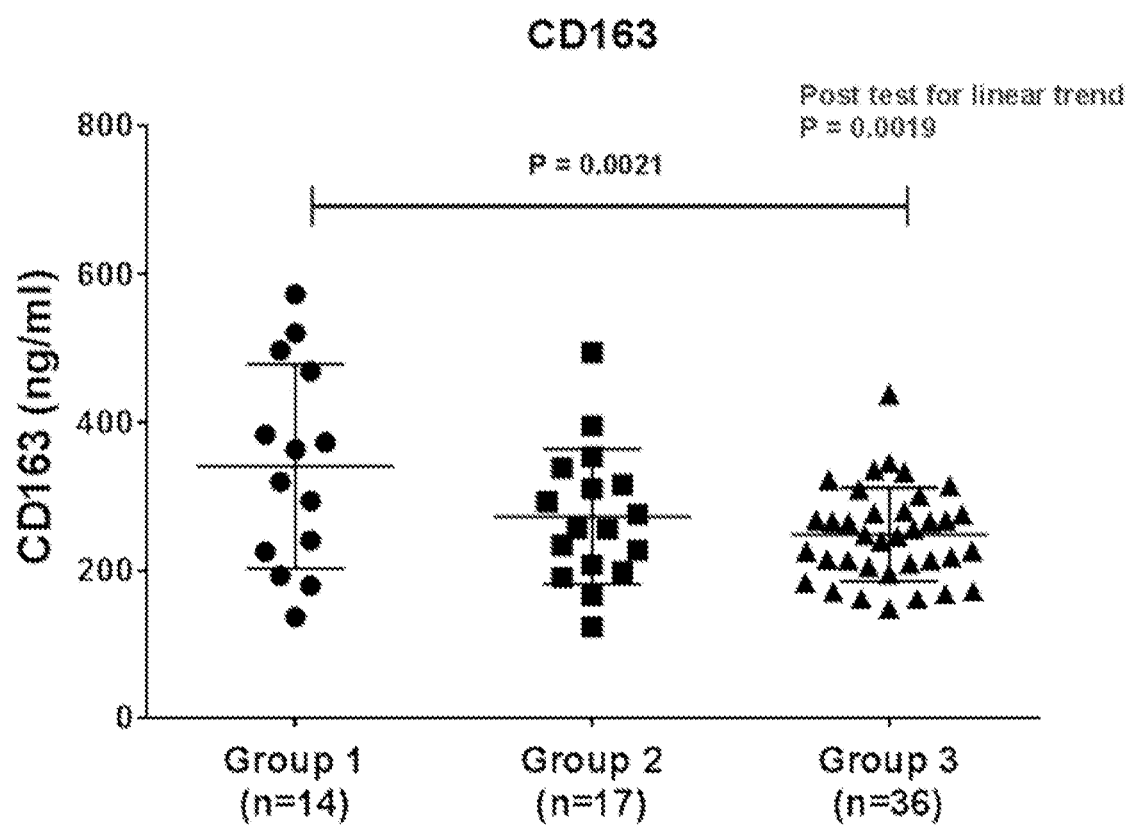
FIG. 4C shows FTD patient plasma has elevated sCD163 consistent with ongoing traffic of monocytes into the CNS.
Figure 4D:
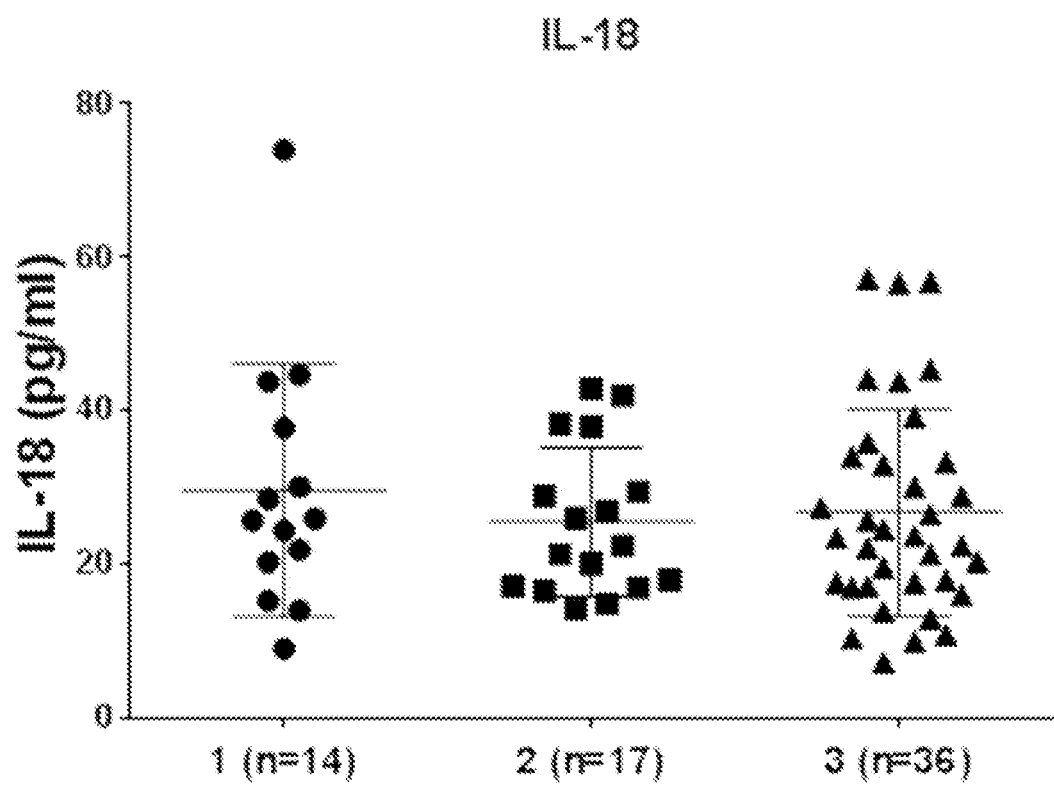
FIG. 4D shows FTD patient plasma levels of IL18.
Figure 4E:
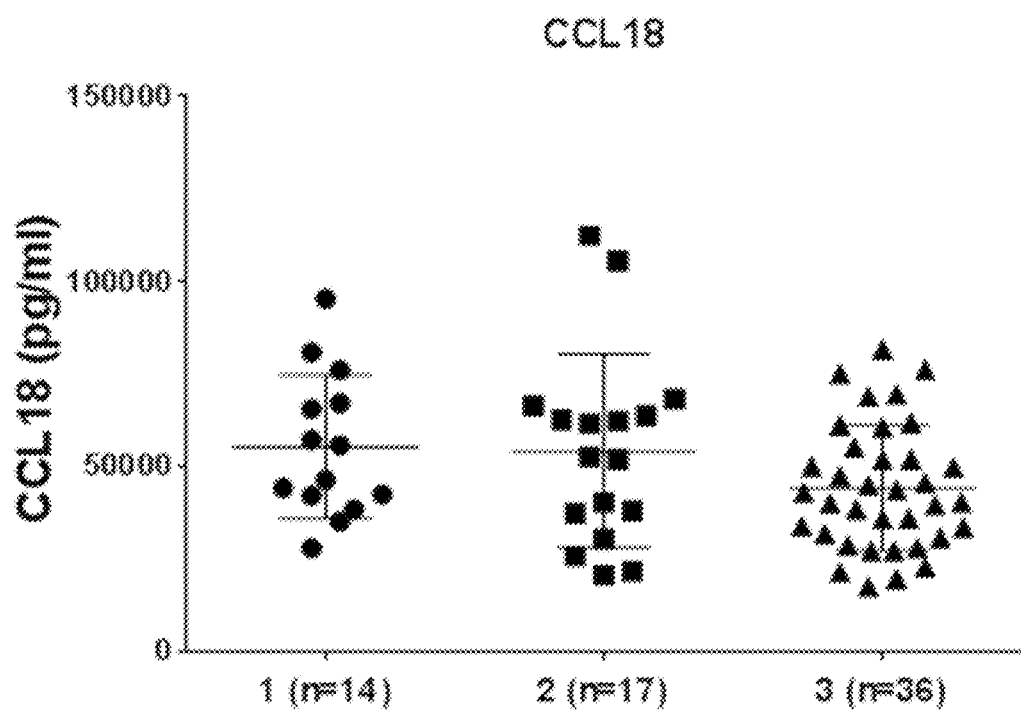
FIG. 4E shows FTD patient plasma levels of CCL18.
Figure 4F:
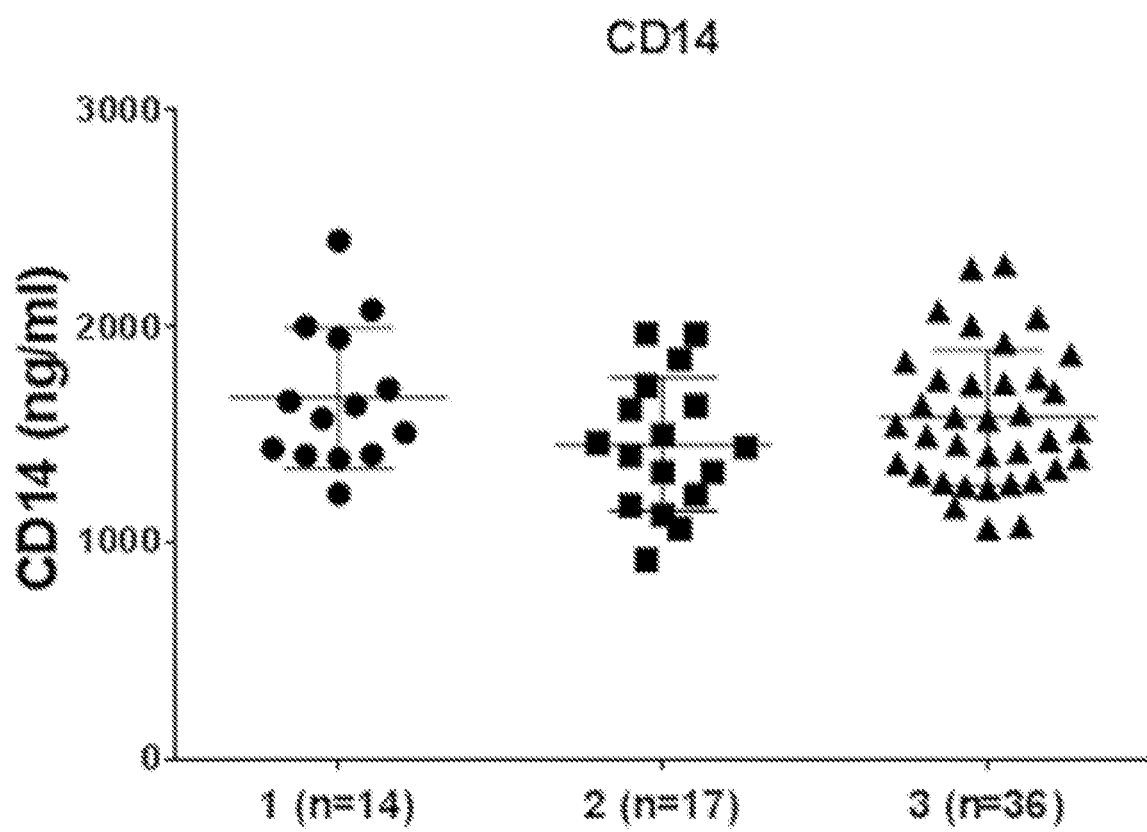
FIG. 4F shows FTD patient plasma levels of CD14.
Figure 4G:
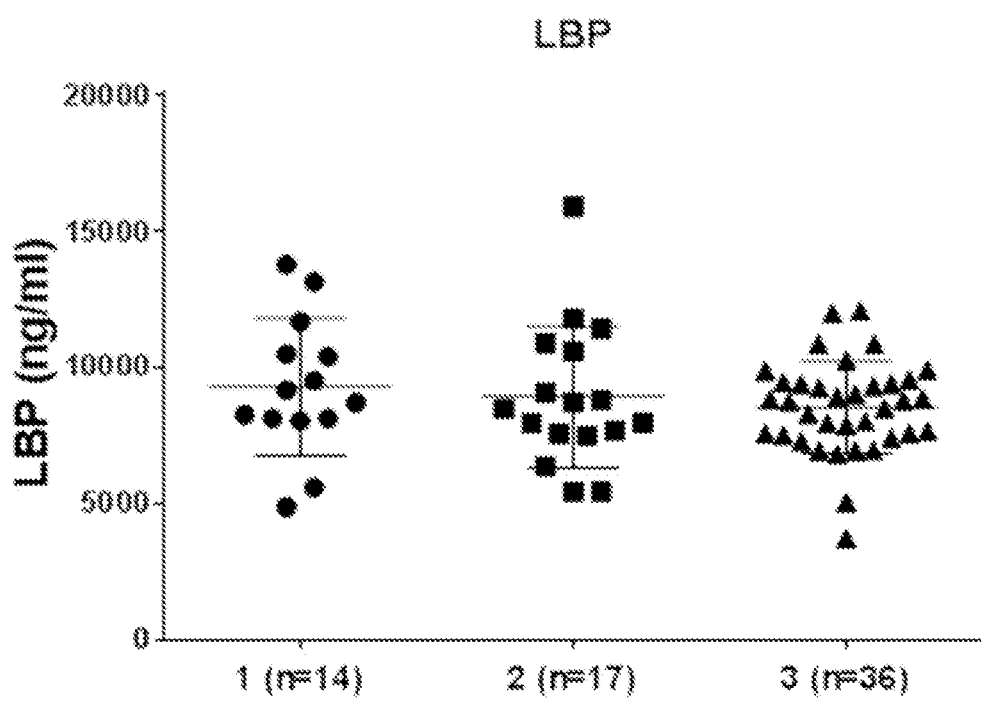
FIG. 4G shows FTD patient plasma levels of LBP.
Figure 5A:
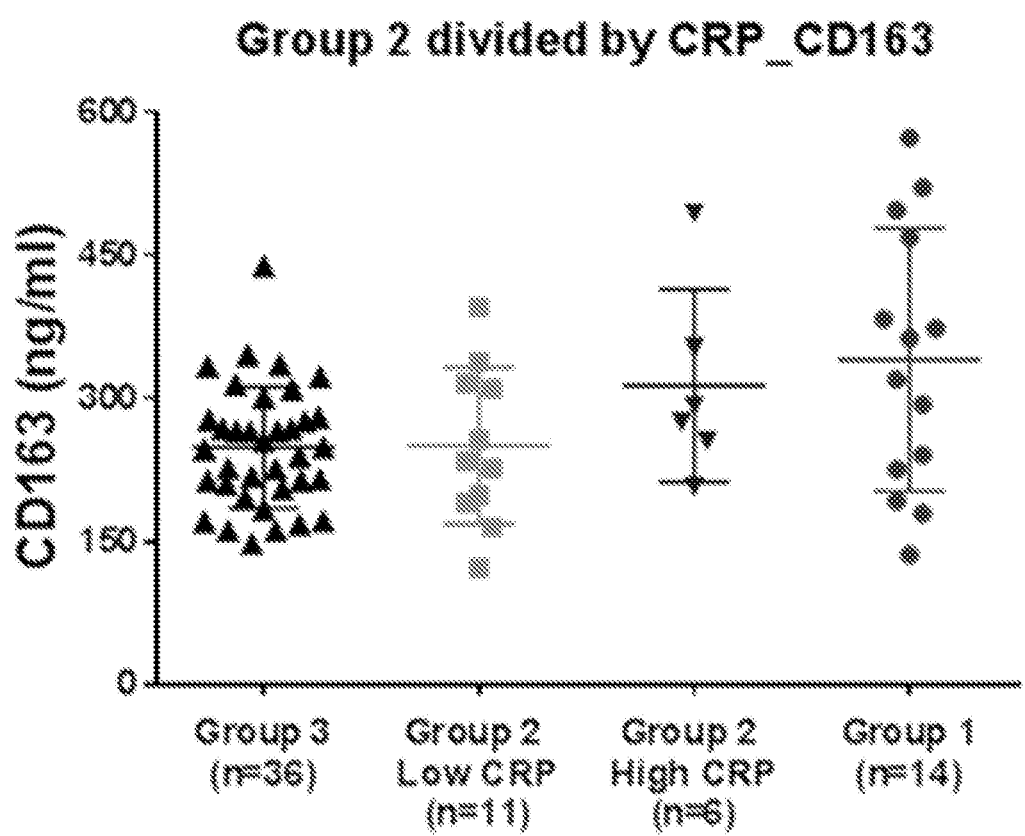
FIG. 5A shows levels of CD163 in plasma from FTD patients heterozygous for the PGN gene (group 1), carriers of a PGN deficiency (group 2, subgroups with low CRP and high CRP), and age matched controls (group 3).
Figure 5B:
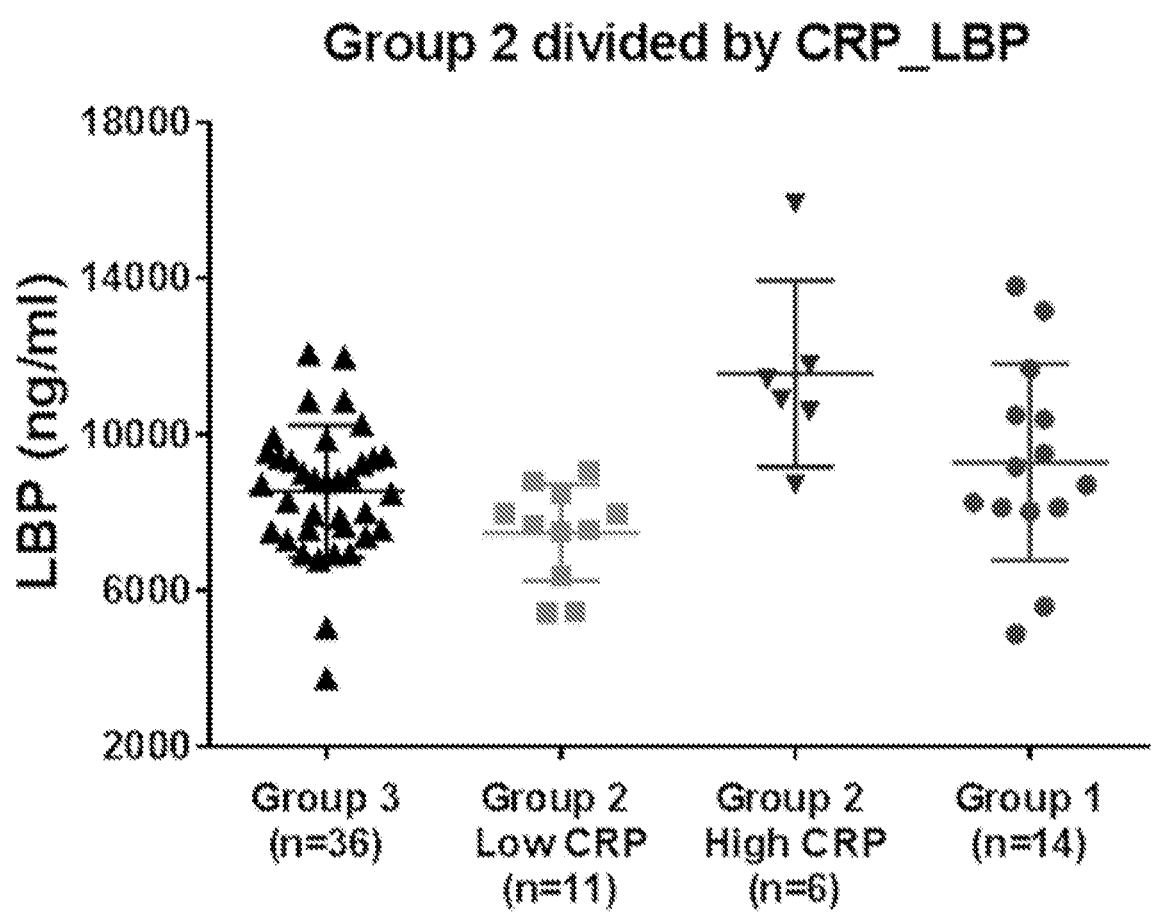
FIG. 5B shows levels of LBP in plasma from FTD patients heterozygous for the PGN gene (group 1), carriers of a PGN deficiency (group 2, subgroups with low CRP and high CRP), and age matched controls (group 3).
Figure 5C:
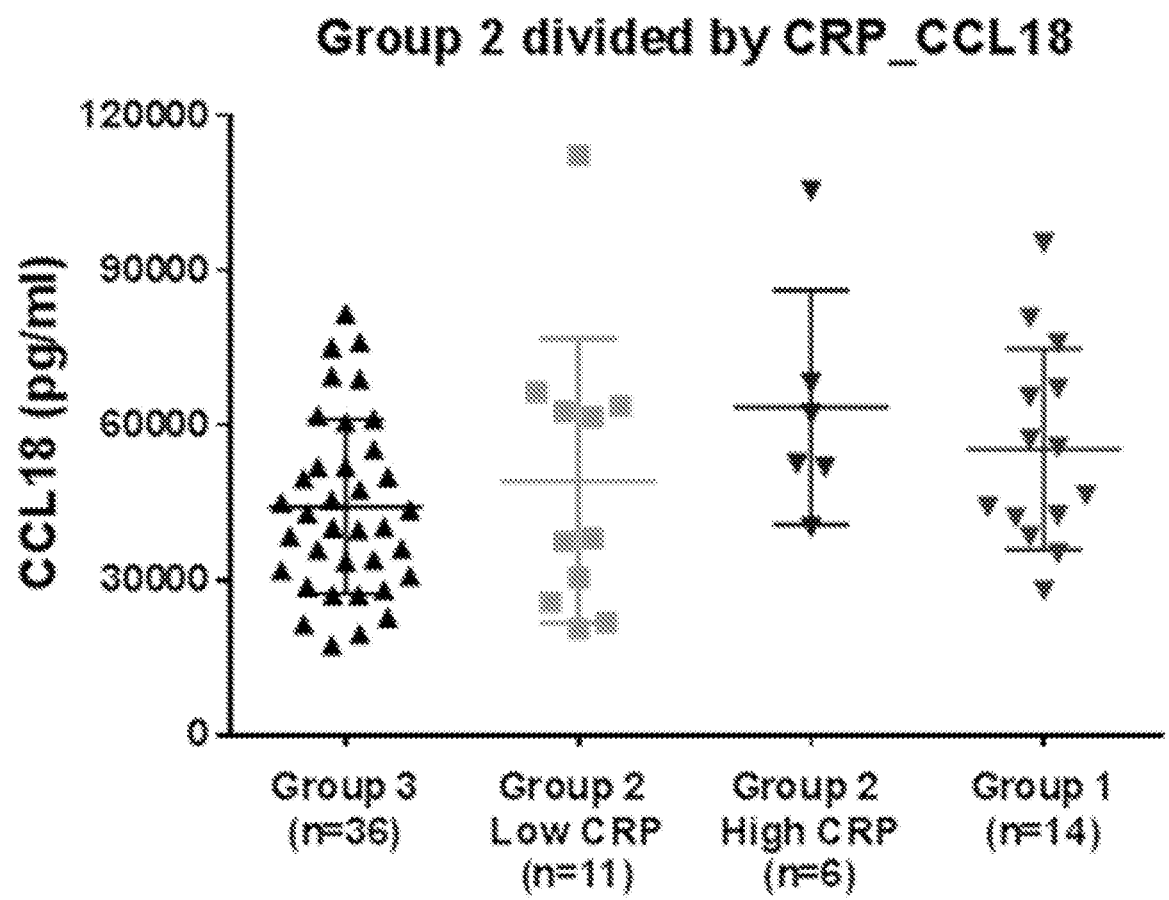
FIG. 5C shows levels of CCL18 in plasma from FTD patients heterozygous for the PGN gene (group 1), carriers of a PGN deficiency (group 2, subgroups with low CRP and high CRP), and age matched controls (group 3).
Figure 5D:
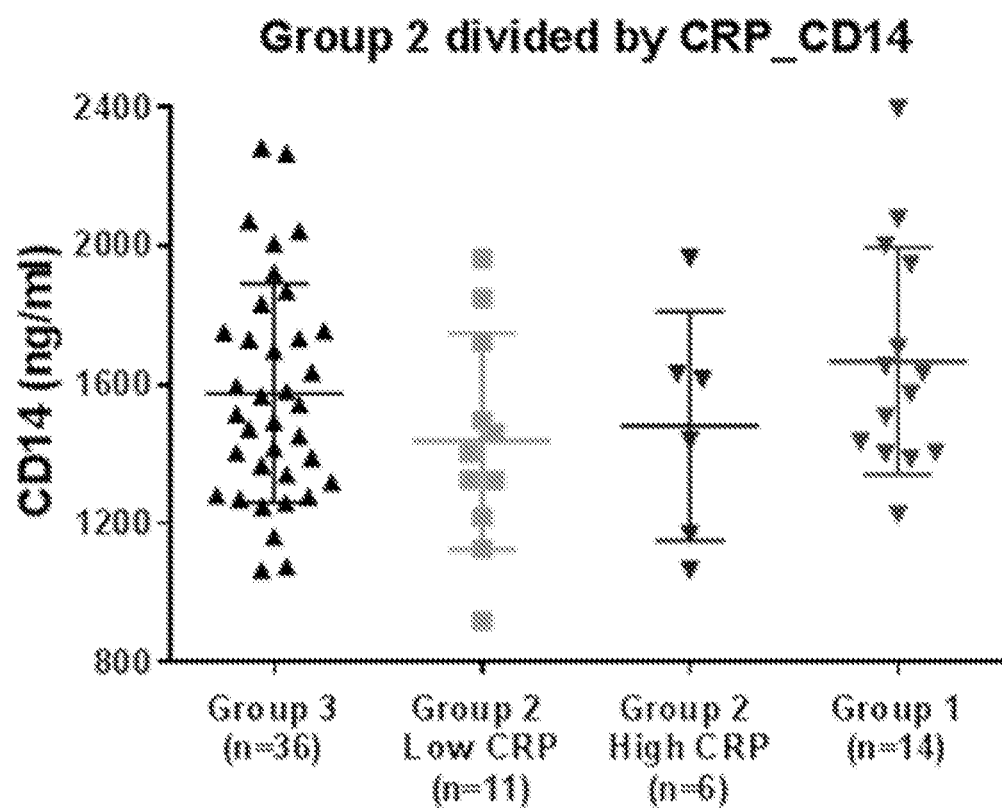
FIG. 5D shows levels of CD14 in plasma from FTD patients heterozygous for the PGN gene (group 1), carriers of a PGN deficiency (group 2, subgroups with low CRP and high CRP), and age matched controls (group 3).
Figure 5E:
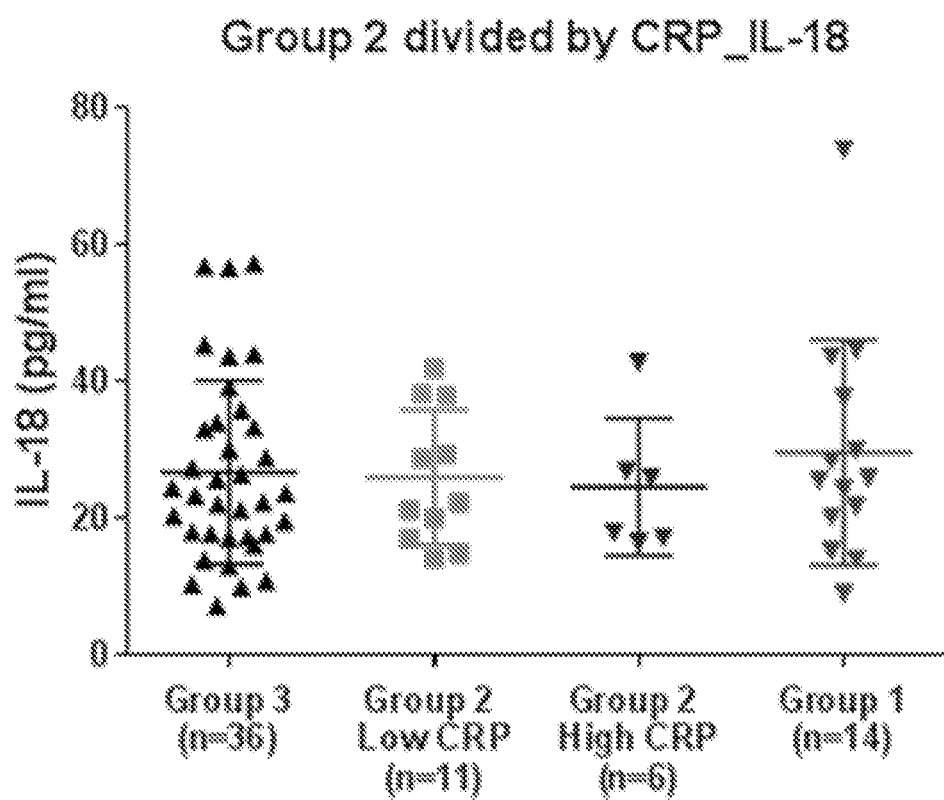
FIG. 5E shows levels of IL18 in plasma from FTD patients heterozygous for the PGN gene (group 1), carriers of a PGN deficiency (group 2, subgroups with low CRP and high CRP), and age matched controls (group 3).

To test whether FTD patients may have plasma factors elevated in comparison to controls, the following experiment was performed: Plasma specimens were obtained from the following groups for ELISA determination of various factor levels: FTD patients heterozygous for the PGN gene (14), Carriers of a PGN deficiency (17), and age matched controls (36). The following factors measured included CRP, IL-18, CCL18, CD14, LBP and CD163 (see FIG. 4A-G).

wr-CRP values in FTD were 2-fold higher than in the 2 control groups (see FIG. 4A). A subset of PGN heterozygous "carriers" (⅓) showed elevation in wr-CRP values similar to values in FTD patients (see FIG. 4B). Using the ALS median value cutoff of 1125 ng/ml, 80% of FTD patients were above the median ALS patient value, consistent with a higher level of inflammation in patients with FTD.

In addition, sCD163 levels were significantly higher in the FTD patient specimens as compared to the controls (see FIG. 4C). sCD163 levels reflect the migration of monocytes from the blood into tissues in models of dementia and presumably in humans with neuroinflammation.

A separate evaluation of the "carriers" between high and low wr-CRP showed the high subset to be similar to the FTD group in sCD163, wr-CRP and LPS binding protein (LBP) levels above all of the other groups (see FIGS. 5A-5E). LBP is upregulated in the presence of systemic LPS or endotoxin, most likely through a process of gut related microbial translocation. The presence of LPS in the plasma of ALS patients was shown in the ALS sodium chlorite phase 2 trial to be associated with more rapid disease progression (ref). In the context of FTD, the presence of elevated LBP in carriers may signify a switching process wherein "carriers" of the PGN mutation may be evolving to a FTD disease state.

Example 3: Immune Phenotype Study of A-T Patients

Heparinized blood from 10 A-T patients and 10 age-and-gender-matched controls was collected. Flow cytometry was used to assess the systemic immune alterations in A-T patients.

Flow cytometry assay: Measure T-cell and monocyte/macrophage cell activation markers, CD14/HLA-DR and CD14/CD16 expression, and CD4/CD38 and CD8/CD38 expression in A-T patients as compared to healthy controls by flow cytometry.

Compared to healthy controls, CD4/CD38 reactivity was significantly lower in patients with A-T, indicating a clear T cell defect in A-T patients.

No difference was found on levels of monocyte activation between A-T patients and healthy controls, but there was a positive correlation of levels of HLA-DR on CD14 monocytes with the age of A-T patients.

Example 4: Evaluate Soluble Inflammatory Factors in A-T Plasma

Test inflammation/activation-related soluble markers in the systemic immune system (plasma or serum) from A-T patients and control groups to find the potential novel biomarkers for A-T disease.

Panel of inflammation/activation-related markers for evaluation in A-T disease: Soluble CD14 (sCD14), Soluble CD163 (sCD163), MCP-1, Osteopontin, C-reactive protein (CRP), and IL-8.

Plasma/serum: Plasma/serum samples are obtained. At least 20 A-T samples and 20 healthy controls are tested to evaluate the soluble inflammatory factors. ELISA assay: Measure plasma/serum levels of soluble inflammatory factors by ELISA kits according to manufacturer's instruction (R & D systems).

Example 5: Treatment with Sodium Chlorite in A-T Disease

Monitor effect on monocyte/macrophage cell activation markers during treatment with sodium chlorite to identify/evaluate the effect of treatment on expression of monocyte cell surface activation markers in A-T disease.

In Vitro A-T PBMC Culture Experiments

Sodium chlorite testing concentration: +0 control and +300 µM sodium chlorite

Culture period: 3-day culture at 37° C. incubator

Flow cytometry assay: Measure monocyte expression of inflammation/activation marker, CD16, after 3-day culture by flow cytometry, and compare CD16 monocyte expression between +0 control and +300 µM sodium chlorite treated samples.

Example 6: Treatment with Sodium Chlorite in A-T Disease

Monitor effect on production of soluble inflammatory factors in vitro to determine the effect of sodium chlorite on the levels of secreted proteins for biomarkers determined by Example 2 with in vitro 3-day culture experiments.

ELISA assay: Measure a variety of soluble factors on 3-day culture A-T supernatants with/without 300 µM sodium chlorite treatment by ELISA kits according to manufacturer's instruction (R & D systems).

Example 7: Treatment with Sodium Chlorite in A-T Disease

Monitor effect of sodium chlorite treatment on gene expression profile of immune activation/inflammatory response pathway to identify/evaluate the effect of sodium chlorite on gene expression profile of immune activation/inflammatory response pathway in A-T disease.

Obtain primary cultures of human peripheral blood mononuclear cells (PBMCs) from A-T patients. Sodium chlorite testing concentration: +0 control and +300 µM sodium chlorite.

Culture period: Overnight culture at 37° C. in a humidified, 5% CO2 incubator.

Gene expression assay: PBMCs are resuspended in Trizol™ after overnight culture (5-10 million cells/1 ml Trizol™) and stored at −80° C. in a freezer for further RNA isolation and gene expression assay.

Example 8: Treatment of Depression with Sodium Chlorite

A patient with depression is injected with a sodium chlorite solution on a weekly basis. Plasma/serum samples are obtained and submitted to a lab-based immunoassay to quantify inflammatory markers in the plasma/serum sample. Inflammatory markers are compared to the patient's pre-treatment levels of plasma/serum inflammatory markers. After treatment, levels of inflammatory markers are reduced. Behavioral and/or neurophysical symptoms of depression are evaluated and found to be reduced as well.

Example 9: Treatment of Bipolar Disorder with Sodium Chlorite

A patient with bipolar disorder is injected with a sodium chlorite solution on a weekly basis. Plasma/serum samples are obtained and submitted to a lab-based immunoassay to quantify inflammatory markers in the plasma/serum sample. Inflammatory markers are compared to the patient's pre-treatment levels of plasma/serum inflammatory markers. After treatment, levels of inflammatory markers are reduced. Behavioral and/or neurophysical symptoms of bipolar disorder are evaluated and found to be reduced as well.

Example 10: Treatment of Schizophrenia with Sodium Chlorite

A patient with schizophrenia is injected with a sodium chlorite solution on a weekly basis. Plasma/serum samples are obtained and submitted to a lab-based immunoassay to quantify inflammatory markers in the plasma/serum sample. Inflammatory markers are compared to the patient's pre-treatment levels of plasma/serum inflammatory markers. After treatment, levels of inflammatory markers are reduced. Behavioral and/or neurophysical symptoms of schizophrenia are evaluated and found to be reduced as well.

Example 11: Treatment of Autism with Sodium Chlorite

A patient with autism is injected with a sodium chlorite solution on a weekly basis. Plasma/serum samples are obtained and submitted to a lab-based immunoassay to quantify inflammatory markers in the plasma/serum sample. Inflammatory markers are compared to the patient's pre-treatment levels of plasma/serum inflammatory markers. After treatment, levels of inflammatory markers are reduced. Behavioral and/or neurophysical symptoms of autism are evaluated and found to be reduced as well.

Example 12: Treatment of Posttraumatic Stress Disorder with Sodium Chlorite

A patient with posttraumatic stress disorder is injected with a sodium chlorite solution on a weekly basis. Plasma/serum samples are obtained and submitted to a lab-based immunoassay to quantify inflammatory markers in the plasma/serum sample. Inflammatory markers are compared to the patient's pre-treatment levels of plasma/serum inflammatory markers. After treatment, levels of inflammatory markers are reduced. Behavioral and/or neurophysical symptoms of posttraumatic stress disorder are evaluated and found to be reduced as well.

Example 13: Treatment of Depression with Sodium Chlorite Based on an Inflammatory Biomarker as a Differential Predictor of Outcome Serum samples from patients with depression are analyzed for an inflammatory marker (for example c-reactive protein). Patients are then randomly assigned to 12-week treatment with sodium chlorite or another antidepressant treatment (for example escitalopram) as in Uher et al. Am J Psychiatry 171:2 (2014) which is incorporated herein by reference. The primary outcome measure is the score on the Montgomer Asberg Depression Rating Scale, administered weekly. This data is used to enable personalized treatment choice based on peripheral blood inflammatory biomarkers.

Example 14: Bioluminescence Analysis of Smad-Dependent TGF-β Signaling in Live Mice Treated with Sodium Chlorite Perturbations of the TGF-β signaling pathway are involved in pathogenesis of many human diseases including neurodegenerative diseases. TGF-β1 helps orchestrate the responses to brain injury and has been implicated in a number of disorders of the central nervous system including stroke, Parkinson's disease, Alzheimer's disease, and brain tumors. Smad-dependent TGF-β signaling is assessed in mouse models of neurodegenerative disease following treatment with sodium chlorite as in Luo and Wyss-Coray, Bioluminescence, Methods in Molecular Biology 574:193-202 (2009), which is incorporated herein by reference. To follow Smad2/3 signaling over time, transgenic reporter mice that express luciferase in response to activation of Smad2/3 (SBE-luc mice) are engineered. After injecting a luciferase substrate, bioluminescence imaging is used to obtain and follow optical signatures in a spatial and temporal manner in living mice. To identify the cellular source of the bioluminescence and signal and because no specific antibodies are available to detect luciferase expression in brain tissue, reporter mice for the TGF-β signaling pathway is used. These SBE-lucRT mice express a trifusion protein containing luciferase, red fluorescent protein (RFP) and thymidine kinase under the control of the same SBE promoter as the original SBE-luc reporter mice. These mice are used to detect TGF-β signaling through (1) a biochemical assay of TGF-β signaling by tissue luciferase; (2) bioluminescence imaging of TGF-β signaling in dissected individual organs; (3) bioluminescence imaging of TGF-β signaling in live animals; and (4) confocal immunofluorescence microscopy to detect which cell type displays activated TGF-β signaling.

Example 15: Treatment of Inflammation, Impaired Host Defense, and Neuropathology with Sodium Chlorite in Progranulin-Deficient Mice Progranulin (PGRN)-deficient mice have exaggerated inflammation, impaired host defense and neuropathology. Mutations in the PGRN gene have been found to cause frontotemporal dementia, the second most common dementia in people under the age of 65. A conditional Pgrn knock-out mouse is used as in Yin et al. J. Exp. Med. 207(1):117-128 (2009), which is incorporated herein by reference. The Pgrn locus is flanked with loxP sites to bracket the promoter and the first four exons in a bacterial artificial chromosome targeting vector. Generation of an all-tissue PGRN knockout is achieved by crossing Pgrn floxed mice with mice transgenic for Cre-recombinase driven by the promoter for the chicken actin gene. The mice used in this study are compared with their WT littermates which are Cre negative. PRGN-deficient mice and their WT littermates are treated with either sodium chlorite or saline. Inflammation is assessed by determining macrophage cytokine levels, age-dependent activation of microglia and astrocytes in the brain; susceptibility to microglial activating agents and oxidative stress; and ubiquitination and phosphorylation of TDP-43 in the brain.

Example 16: Treatment of Alzheimer's Disease Mouse Models with Sodium Chlorite

An elevated proinflammatory state contributes to the pathogenesis of neurodegenerative diseases, including Alzheimer's disease. PRGN levels are upregulated in the microglia surrounding plaques in patients with Alzheimer's disease. Transgenic APP mice (an Alzheimer's disease mouse model) are used as in Minami et al. Nat Med 20(10):1157-1167 (2014) which is incorporated herein by reference. Mice are treated with sodium chlorite. Levels of PRGN expression are measured in treated and untreated mice. AD dependent cognitive deficits, innate immune responses, plaque deposition, and microglial phagocytosis are also measured.

Example 17: Treatment of Parkinson's Disease Mouse Models with Sodium Chlorite

Brain inflammation induced by peripheral inflammatory signals contributes to the pathogenesis of neurodegenerative diseases, including Parkinson's disease. TGFβ-luciferase reporter mice (TGFβ-luc) are used as in Luo et al. Proc Natl Acad Sci 103(48):18326-31 (2006) which is incorporated herein by reference. TGFβ-luc mice display time-dependent brain inflammation induced by peripheral lipopolysaccharide (LPS) and are used to determine the dose-dependent modulation of the CNS inflammatory signal by treatment with sodium chlorite. Bioluminescence signal in the brains of TGFβ-luc mice is induced by systemic injection of 5 mg/kg LPS along with intravenous doses of 0, 0.5, 1.5, 4.5 or 13.5 mg/kg sodium chlorite. Mice are imaged 6-18 hours following LPS administration and the dose-dependent attenuation of inflammatory signal in response to the sodium chlorite treatment is determined and compared to dosing with the vehicle.

A month later, TGFβ-luc mice are injected with 5 mg/kg LPS again followed by intravenous doses of 0, 0.5, 1.5, 4.5 or 13.5 mg/kg sodium chlorite at the peak of the light signal (6-8 hrs post LPS) and are imaged 1-2 hrs later. Sodium chlorite treatment is compared to the drug vehicle injection to establish the speed with which the signal is brought down. Immediately after the bioluminescence studies, mice with one or the other LPS/sodium chlorite dosing paradigm are sacrificed for collection of peripheral blood and brain tissue for histological, biochemical and molecular assessment of inflammation.

Example 18: Treatment of Parkinson's Disease Mouse Models with Sodium Chlorite

Overexpression of ha-synuclein in the substantia nigra of mice leads to microglia activation and loss of dopaminergic neuron and their striatal projections causing neuroinflammation and neurodegeneration. This contributes to the pathogenesis of neurodegenerative diseases, including Parkinson's disease. TGFβ-luc mice are used to determine the therapeutic efficacy of sodium chlorite against neuroinflammation and neurodegeneration induced by rAAV2/5-hα-synuclein. Sodium chlorite is administered daily intravenously into TGFβ-Luc mice that receive a unilateral intranigral AAV2-hASyn virus injection via stereotaxic surgery starting one week after virus injection at 0, 0.5, 3.2 or 10 mg/kg for a minimum of 5 days/week to maintain the bioluminescence signal attenuated. Mice are imaged weekly for 2 months (=peak of microglia activation) and monthly thereafter until age 6 months (=peak of dopaminergic degeneration) post rAAV5-hα-synuclein to monitor the effect of sodium chlorite treatment on the magnitude and duration of brain inflammation induced by rAAV5-hα-synuclein. The frequency of sodium chlorite dosing is dictated by the duration of bioluminescence signal attenuation. For comparison purposes, optimal dosing in man was every three weeks.

To determine the ability of sodium chlorite treatment to modulate hAsyn-induced microglia activation, cytokine production and protect against nigral dopaminergic neuron degeneration, half of the mice at the 2-month timepoint are sacrificed after bioluminescence for analyses of brain microglia and infiltrating monocytes by flow cytometry and circulating inflammatory factors in plasma by multiplexed immunoassay. At 6-month timepoint, the rest of the mice are perfused-fixed for immunohistological analysis of synuclein pathology, nigral TH+/NeuN+ neurons, microgliosis and astrocytosis to determine the neuroprotective effects of sodium chlorite on rAAV2/5-hα-synuclein-induced degeneration.

Example 19: Toxicity and Proof of Biology Studies with Sodium Chlorite in Human Peripheral Monocytes GG homozygosity at rs3129882 in the human MHC-II HLA-DRA locus is associated with increased baseline MHC-II surface protein and heightened inducibility of MHC-II gene expression in Parkinson's disease patients relative to age-matched healthy controls. The immunomodulatory effects of ex vivo sodium chlorite treatment is determined by determining the switch of M1 phenotype (as evidenced by heightened inducibility of MHC-II expression and expression/secretion of pro-inflammatory cytokines) towards an M2 phenotype in peripheral monocytes from Parkinson's disease patients. Heparinized peripheral blood from individuals with Parkinson's disease homozygous for the GG genotype at the rs3129882 HLA-DRA SNP is collected by venipuncture for isolation of PBMCs. Monocytes are purified from the PBMCs using CD14-specific paramagnetic bead isolation kits that result in >90% purity. A range of IFNγ (10-1000 U/ml) is used to induce MHC-II surface expression and the objective is to determine the ability of sodium chlorite to dose-dependently decrease this heightened inducibility of MHC-II. Surface expression of MHC-II molecules is measured by multi-parameter flow cytometry on peripheral monocytes (treated +/−IFNγ) as is intracellular cytokine staining (ICS) for pro- and anti-inflammatory cytokines (TNF, IL-6, IL1β, IL-10, TGFβ).

Figure 6:
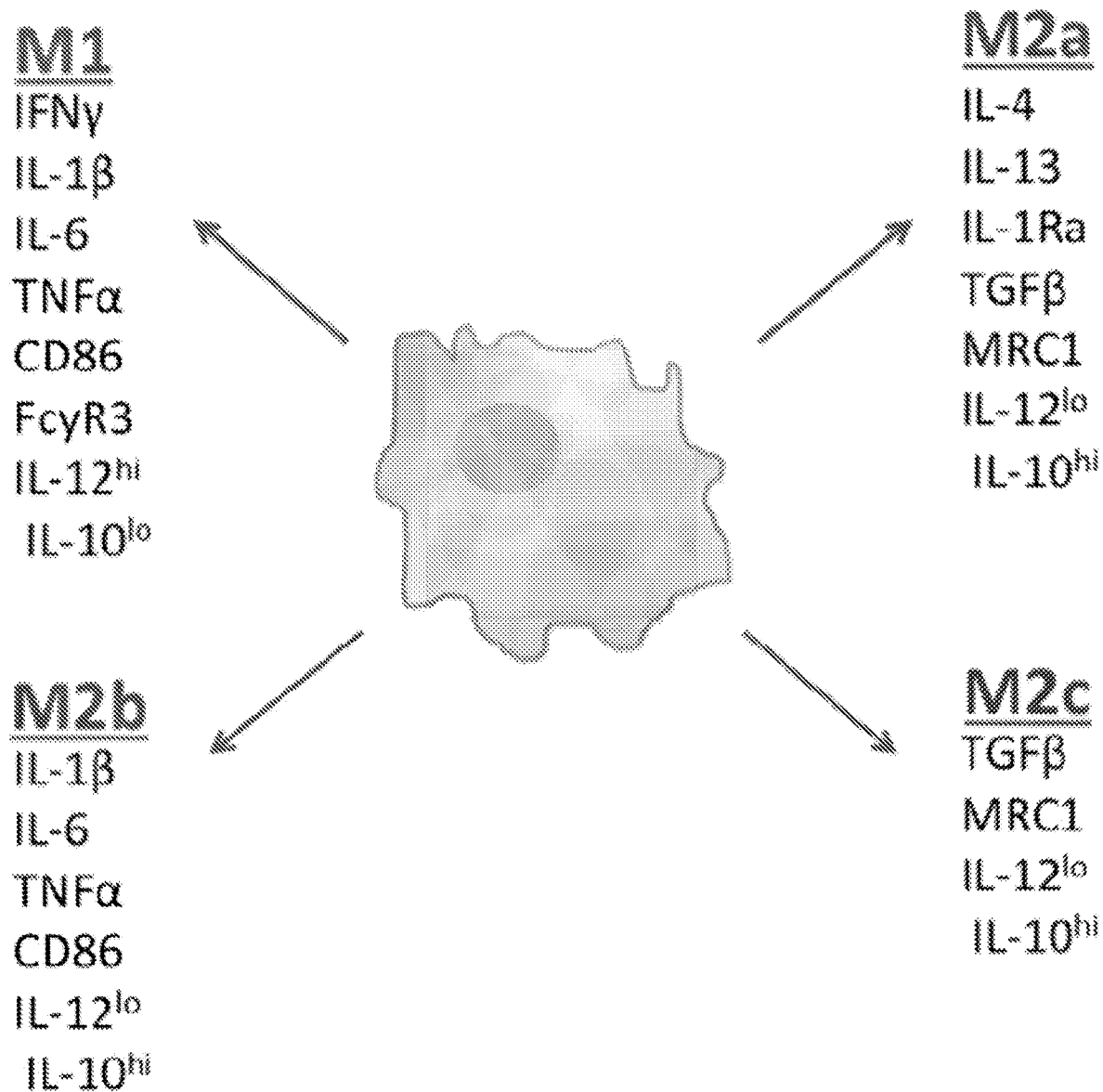
FIG. 6 exemplifies the characteristic gene expression of monocyte/macrophages displaying M1/M2 polarization.

Monocytes are also plated and treated with a range of IFNγ for 16 hours to assess the ability of these cells to up-regulate MHC-II gene expression plus or minus sodium chlorite (or saline vehicle). A range of IFNγ (10-1000 U/ml) is used to induce MHC-II gene expression and the ability of sodium chlorite to dose-dependently decrease inducibility of heightened MHC-II expression. FIG. 6 exemplifies the inflammatory markers—expression of which is analyzed to assess the monocyte/macrophage M1/M2 polarization state. Conditioned media is collected from the plated cells for measurements of secreted inflammatory factors (TNF, IL1β, IL-2, IL-4, IL-6, IL-8, IL-10, TGFβ, IL-12p70, IL-13, and IFNγ) by multiplexed immunoassay on the Meso Scale Discovery platform, and for phagocytosis of fluorescent *E. coli* particles and fluorescently-labeled aggregated human α-synuclein.

Example 20: Treatment of Neurodegenerative Mouse Models with Sodium Chlorite

NADPH oxidase (NOX) is a series of enzymes that are involved in producing ROS. Studies in mixed neuronal-glial cultures have found that NOX2 contributes to ROS formation, microglial activation and dopamine neuron degeneration. NOX2−/− mice are generated which lack a functional GP91 protein, an X chromosome gene that contains the catalytic subunit of the NOX complex as in Qin et al., Glia 61(6): 855-868 (2013) which is incorporated herein by reference. Lipopolysaccharide is used to induce neuroimmune activation of microglia in NOX2-deficient mice. Mice are then treated with sodium chlorite and microglial activation morphology and ROS formation is measured. Loss of dopaminergic neurons is assessed by counting the number of TH+ immunoreactive neurons in the substantia nigra pars compacta. In situ visualization of O2- and O2-derived oxidant (ROS) production is assessed by hydroethidine histochemistry. Brains are also assayed using an ELISA for TNF-α, IL-1-β, and MCP-1.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   a) administering to a subject who has dementia a regimen of sodium chlorite; and
   b) monitoring a plasma level of C-reactive protein in the subject during the regimen of sodium chlorite and determining based on the monitoring that the plasma level of C-reactive protein in the subject is at least 1125 ng/mL.

2. The method of claim 1, wherein the administering is parenteral.

3. The method of claim 1, wherein the administering is intravenous.

4. The method of claim 1, wherein the administering occurs over a period ranging from about 0.5 to about 4 hours.

5. The method of claim 1, wherein the administering occurs at least once per month for a period of at least a year.

6. The method of claim 1, wherein the administering occurs at least once per week for a period of at least one month.

7. The method of claim 1, wherein the sodium chlorite is administered in an amount ranging from 0.1 to 10 mg/kg by body weight.

8. The method of claim 1, wherein the sodium chlorite is administered in an amount ranging from 1 to 2 mg/kg by body weight.

9. The method of claim 1, wherein the monitoring the plasma level of C-reactive protein in the subject during the regimen of sodium chlorite comprises detecting the C-reactive protein in a biological sample of the subject.

10. The method of claim 1, wherein the monitoring the plasma level of C-reactive protein in the subject during the regimen of sodium chlorite comprises quantifying the C-reactive protein in a biological sample of the subject.

11. The method of claim 1, wherein the dementia is Amyotrophic Lateral Sclerosis (ALS).

12. The method of claim 1, wherein the subject exhibits a behavioral symptom of the dementia.

13. The method of claim 1, wherein the subject exhibits a physical symptom of the dementia.

14. The method of claim 1, wherein the subject is human.

\* \* \* \* \*